(12) United States Patent
Bander et al.

(10) Patent No.: US 10,517,969 B2
(45) Date of Patent: Dec. 31, 2019

(54) METHODS AND KITS FOR DIAGNOSIS OF CANCER AND PREDICTION OF THERAPEUTIC VALUE

(75) Inventors: Neil H. Bander, Chappaqua, NY (US); Joseph Osborne, New York, NY (US); Stanley J. Goldsmith, Floral Park, NY (US); Shankar Vallabhajosula, Larchmont, NY (US)

(73) Assignee: CORNELL UNIVERSITY, Ithaca, NY (US)

( * ) Notice: Subject to any disclaimer, the term of this patent is extended or adjusted under 35 U.S.C. 154(b) by 0 days.

(21) Appl. No.: 12/658,881

(22) Filed: Feb. 17, 2010

(65) Prior Publication Data

US 2010/0209343 A1 Aug. 19, 2010

Related U.S. Application Data

(60) Provisional application No. 61/153,132, filed on Feb. 17, 2009.

(51) Int. Cl.
| | | |
|---|---|---|
| *A61K 49/00* | (2006.01) | |
| *A61K 51/10* | (2006.01) | |
| *A61K 51/08* | (2006.01) | |

(52) U.S. Cl.
CPC ................. *A61K 51/106* (2013.01)

(58) Field of Classification Search
CPC ........ A61K 38/00; A61K 38/02; A61K 49/10; A61K 49/101; A61K 49/12; A61K 49/14; A61K 49/16; A61K 49/004; A61K 49/0008; A61K 49/085; A61K 49/00; A61K 49/08; A61K 2123/00; A61K 2121/00; A61K 39/0011; A61K 39/00; A61K 2039/505; A61K 51/00; A61K 51/04; A61K 51/02; A61K 51/0474; A61K 51/06; A61K 51/065; A61K 51/1093; A61K 51/10; A61K 51/08; A61K 51/0497; A61K 51/0406; A61K 51/106; A61K 51/0482; G01N 2800/52
USPC .......... 424/1.11, 1.49, 1.65, 1.69, 1.73, 1.81, 424/1.85, 1.89, 9.1, 9.2, 9.3, 9.4, 9.5, 9.6, 424/9.7, 9.8; 514/1, 1.11, 1.1
See application file for complete search history.

(56) References Cited

U.S. PATENT DOCUMENTS

| | | |
|---|---|---|
| 4,892,824 A | 1/1990 | Skaletsky |
| 4,943,525 A | 7/1990 | Dawson |
| 5,120,525 A | 6/1992 | Goldenberg et al. |
| 5,162,504 A | 11/1992 | Horoszewicz |
| 5,208,020 A | 5/1993 | Chari et al. |
| 5,256,395 A | 10/1993 | Barbet et al. |
| 5,332,567 A | 7/1994 | Goldenberg |
| 5,376,249 A | 12/1994 | Afeyan et al. |
| 5,475,092 A | 12/1995 | Chari et al. |
| 5,518,889 A | 5/1996 | Lander et al. |
| 5,523,210 A | 6/1996 | Paulus |
| 5,525,338 A * | 6/1996 | Goldenberg ............... 424/178.1 |
| 5,530,101 A | 6/1996 | Queen et al. |
| 5,534,254 A | 7/1996 | Huston et al. |
| 5,538,866 A | 7/1996 | Israeli et al. |
| 5,582,996 A | 12/1996 | Curtis |
| 5,585,499 A | 12/1996 | Chari et al. |
| 5,591,828 A | 1/1997 | Bosslet et al. |
| 5,627,078 A | 5/1997 | Karl et al. |
| 5,637,481 A | 6/1997 | Ledbetter et al. |
| 5,688,690 A | 11/1997 | Valiante et al. |
| 5,693,477 A | 12/1997 | Cornell et al. |
| 5,705,614 A | 1/1998 | Ring |
| 5,712,136 A | 1/1998 | Wickham et al. |
| 5,747,035 A | 5/1998 | Presta et al. |
| 5,762,930 A | 6/1998 | Fanger et al. |
| 5,821,333 A | 10/1998 | Carter et al. |
| 5,830,473 A | 11/1998 | Thierfelder |
| 5,830,478 A | 11/1998 | Raso et al. |
| 5,837,242 A | 11/1998 | Holliger et al. |
| 5,837,821 A | 11/1998 | Wu |
| 5,840,854 A | 11/1998 | Hellstrom et al. |
| 5,844,094 A | 12/1998 | Hudson et al. |
| 5,846,545 A | 12/1998 | Chari et al. |
| 5,851,527 A | 12/1998 | Hansen |
| 5,852,186 A | 12/1998 | Sodroski et al. |
| 5,861,156 A | 1/1999 | George et al. |
| 5,863,765 A | 1/1999 | Berry et al. |
| 5,869,049 A | 2/1999 | Noelle et al. |
| 5,869,053 A | 2/1999 | Stern et al. |
| 5,869,620 A | 2/1999 | Whitlow et al. |
| 5,876,691 A | 3/1999 | Chester et al. |
| 5,877,291 A | 3/1999 | Mezes et al. |
| 5,932,448 A | 8/1999 | Tso et al. |
| 5,935,818 A | 8/1999 | Israeli et al. |
| 5,942,229 A | 8/1999 | Noelle et al. |

(Continued)

FOREIGN PATENT DOCUMENTS

| | | |
|---|---|---|
| EP | 0668777 | 8/1995 |
| EP | 0 956 506 | 7/1996 |

(Continued)

OTHER PUBLICATIONS

Golub et al, Science, Oct. 15, 1999, pp. 531-537.*

(Continued)

*Primary Examiner* — D. L. Jones
(74) *Attorney, Agent, or Firm* — Proskauer Rose LLC; James H. Shalek; Sang-A Kim

(57) ABSTRACT

A method for identifying a patient for cancer therapy can include administering a diagnostic dose of a detectably labeled first binding agent to a patient, the detectably labeled binding agent being capable of binding a molecular target. The method also includes selecting a patient for administration of a therapeutic dose of a second binding agent capable of binding a cellular target, wherein the selected patient exhibits a positive reading for the detectably labeled first binding agent. Furthermore, the method can include administering a therapeutic dose of the second binding agent to the patient.

9 Claims, 15 Drawing Sheets
(4 of 15 Drawing Sheet(s) Filed in Color)

(56) References Cited

U.S. PATENT DOCUMENTS

| | | |
|---|---|---|
| 5,951,982 A | 9/1999 | Zöller et al. |
| 5,959,083 A | 9/1999 | Bosslet et al. |
| 5,972,615 A * | 10/1999 | An et al. ............. 435/6.14 |
| 5,980,896 A | 11/1999 | Hellstrom et al. |
| 5,989,830 A | 11/1999 | Davis et al. |
| 5,990,275 A | 11/1999 | Whitlow et al. |
| 6,010,902 A | 1/2000 | Ledbetter et al. |
| 6,030,792 A | 2/2000 | Otterness et al. |
| 6,071,490 A | 6/2000 | Griffiths et al. |
| 6,083,763 A | 7/2000 | Balch |
| 6,096,871 A | 8/2000 | Presta et al. |
| 6,099,841 A | 8/2000 | Hillan et al. |
| 6,107,090 A | 8/2000 | Bander |
| 6,121,022 A | 9/2000 | Presta et al. |
| 6,136,311 A | 10/2000 | Bander |
| 6,150,508 A | 11/2000 | Murphy et al. |
| 6,193,966 B1 | 2/2001 | Deo et al. |
| 6,197,298 B1 | 3/2001 | Chang |
| 6,200,765 B1 | 3/2001 | Murphy et al. |
| 6,201,167 B1 | 3/2001 | Pothier |
| 6,241,961 B1 | 6/2001 | Benes et al. |
| 6,248,516 B1 | 6/2001 | Winter et al. |
| 6,284,742 B1 | 9/2001 | Curiel et al. |
| 6,294,391 B1 | 9/2001 | Badley et al. |
| 6,312,694 B1 | 11/2001 | Thorpe et al. |
| 6,329,503 B1 | 12/2001 | Afar et al. |
| 6,340,701 B1 | 1/2002 | Chari et al. |
| 6,342,219 B1 | 1/2002 | Thorpe et al. |
| 6,342,587 B1 | 1/2002 | Barbas, III et al. |
| 6,361,774 B1 | 3/2002 | Griffiths et al. |
| 6,368,596 B1 | 4/2002 | Ghetie et al. |
| 6,383,759 B1 | 5/2002 | Murphy et al. |
| 6,387,350 B2 | 5/2002 | Goldenberg |
| 6,399,068 B1 | 6/2002 | Godlenberg |
| 6,458,933 B1 | 10/2002 | Hansen |
| 6,492,123 B1 | 12/2002 | Hollinger et al. |
| 6,569,432 B1 | 5/2003 | Israeli et al. |
| 6,602,684 B1 | 8/2003 | Umana et al. |
| 6,649,163 B1 | 11/2003 | Bander |
| 6,709,844 B1 | 3/2004 | Levy |
| 6,767,711 B2 | 7/2004 | Bander |
| 6,770,450 B1 | 8/2004 | Bander |
| 6,824,780 B1 | 11/2004 | Devaux et al. |
| 6,833,438 B1 | 12/2004 | Afar et al. |
| 6,835,866 B1 | 12/2004 | Mangelsdorf et al. |
| 6,861,234 B1 | 3/2005 | Simard et al. |
| 6,869,620 B2 | 3/2005 | Moore |
| 6,870,034 B2 | 3/2005 | Breece et al. |
| 6,887,975 B2 | 5/2005 | Afar et al. |
| 6,953,668 B1 | 10/2005 | Israeli et al. |
| 6,962,981 B1 | 11/2005 | Murphy et al. |
| 6,972,324 B2 | 12/2005 | Adolf et al. |
| 6,977,074 B2 | 12/2005 | Kundig et al. |
| 6,994,851 B1 | 2/2006 | Kundig et al. |
| 7,037,647 B1 | 5/2006 | Israeli et al. |
| 7,045,605 B2 | 5/2006 | Bander et al. |
| 7,045,608 B2 | 5/2006 | Eliu et al. |
| 7,053,186 B2 | 5/2006 | Afar et al. |
| 7,070,782 B1 | 7/2006 | Israeli et al. |
| 7,105,159 B1 | 9/2006 | Israeli et al. |
| 7,112,412 B1 | 9/2006 | Bander |
| 7,163,680 B2 | 1/2007 | Bander |
| 7,166,714 B2 | 1/2007 | Afar et al. |
| 7,192,586 B2 | 3/2007 | Bander |
| 7,232,682 B2 | 6/2007 | Simard et al. |
| 7,235,641 B2 | 6/2007 | Kufer et al. |
| 7,319,006 B2 | 1/2008 | Afar et al. |
| 7,323,553 B2 | 1/2008 | Fahrner et al. |
| 7,364,729 B2 | 4/2008 | Kundig et al. |
| 7,375,078 B2 | 5/2008 | Feng |
| 7,390,654 B2 | 6/2008 | Levy |
| 7,399,461 B2 | 7/2008 | Heston et al. |
| 7,435,416 B2 | 10/2008 | Devaux et al. |
| 7,452,539 B2 | 11/2008 | Emery et al. |
| 7,455,991 B2 | 11/2008 | Afar et al. |
| 7,468,354 B2 * | 12/2008 | Isaacs et al. ............. 514/1.1 |
| 7,485,299 B2 | 2/2009 | Afar et al. |
| 7,485,704 B2 | 2/2009 | Fahrner et al. |
| 7,494,646 B2 | 2/2009 | Jakobovits et al. |
| 7,498,298 B2 | 3/2009 | Doronina et al. |
| 7,514,078 B2 | 4/2009 | Bander et al. |
| 7,517,670 B2 | 4/2009 | Umana et al. |
| 7,521,541 B2 | 4/2009 | Eigenbrot et al. |
| 7,524,813 B2 | 4/2009 | Zundel et al. |
| 7,541,441 B2 | 6/2009 | Rosen et al. |
| 7,575,749 B2 | 8/2009 | Afar et al. |
| 7,595,379 B2 | 9/2009 | Gudas et al. |
| 7,611,904 B2 | 11/2009 | Afar et al. |
| 7,612,181 B2 | 11/2009 | Wu et al. |
| 7,622,569 B2 | 11/2009 | Raitano et al. |
| 7,642,054 B2 | 1/2010 | Afar et al. |
| 7,662,936 B2 | 2/2010 | Kadkhodayan et al. |
| 7,666,414 B2 | 2/2010 | Bander |
| 7,666,425 B1 | 2/2010 | Bander |
| 7,727,533 B2 | 6/2010 | Afar et al. |
| 7,745,394 B2 | 6/2010 | Doronina et al. |
| 7,754,681 B2 | 7/2010 | Feng |
| 7,771,953 B2 * | 8/2010 | Ross ............. 435/7.1 |
| 7,807,799 B2 | 10/2010 | Fahrner et al. |
| 7,820,166 B2 | 10/2010 | Lanzavecchia |
| 7,838,637 B2 | 11/2010 | Kontermann et al. |
| 7,855,275 B2 | 12/2010 | Eigenbrot et al. |
| 7,867,483 B2 | 1/2011 | Delcayre et al. |
| 7,884,179 B2 | 2/2011 | Faris et al. |
| 7,888,035 B2 | 2/2011 | Klass et al. |
| 7,897,356 B2 | 3/2011 | Klass et al. |
| 7,906,329 B2 | 3/2011 | Umana et al. |
| 7,928,201 B2 | 4/2011 | Afar et al. |
| 7,939,503 B2 | 5/2011 | Jakobovits et al. |
| 7,947,276 B2 | 5/2011 | Jakobovits et al. |
| 7,947,459 B2 | 5/2011 | Hubert et al. |
| 7,947,839 B2 | 5/2011 | Gazzard et al. |
| 7,960,109 B2 | 6/2011 | Hessels et al. |
| 7,964,566 B2 | 6/2011 | Doronina et al. |
| 7,964,567 B2 | 6/2011 | Doronina et al. |
| 7,968,307 B2 | 6/2011 | Afar et al. |
| 7,989,434 B2 | 8/2011 | Feng |
| 7,994,135 B2 | 8/2011 | Doronina et al. |
| 7,998,701 B2 | 8/2011 | Chua et al. |
| 8,007,994 B2 | 8/2011 | Mangelsdorf et al. |
| 8,008,442 B2 | 8/2011 | Jakobovits et al. |
| 8,012,937 B2 | 9/2011 | Raitano et al. |
| 8,013,128 B2 | 9/2011 | Gudas et al. |
| 8,013,135 B2 | 9/2011 | Jakobovits et al. |
| 8,206,932 B2 | 6/2012 | Gudas |
| 8,278,424 B2 | 10/2012 | Gudas |
| 2002/0004215 A1 | 1/2002 | Osbourn et al. |
| 2002/0018749 A1 | 2/2002 | Hudson et al. |
| 2002/0037289 A1 | 3/2002 | Thorpe et al. |
| 2002/0119096 A1 | 8/2002 | Griffiths |
| 2002/0119153 A1 | 8/2002 | Thorpe et al. |
| 2002/0132979 A1 | 9/2002 | Chen |
| 2002/0136689 A1 | 9/2002 | Reiter et al. |
| 2003/0118583 A1 | 6/2003 | Emery et al. |
| 2003/0170228 A1 | 9/2003 | Ashkenazi et al. |
| 2003/0175900 A1 | 9/2003 | Ashkenazi et al. |
| 2003/0211096 A1 | 11/2003 | Ashkenazi et al. |
| 2004/0018519 A1 | 1/2004 | Wright |
| 2004/0033511 A1 | 2/2004 | Pfizenmaier et al. |
| 2004/0038339 A1 | 2/2004 | Kufer et al. |
| 2004/0071690 A1 | 4/2004 | Hudson et al. |
| 2004/0162411 A1 | 8/2004 | Lanzavecchia |
| 2004/0241817 A1 | 12/2004 | Umana et al. |
| 2005/0026178 A1 | 2/2005 | Nilsen-Hamilton |
| 2005/0136050 A1 | 6/2005 | Kufer et al. |
| 2005/0175618 A1 | 8/2005 | Carroll et al. |
| 2005/0215769 A1 | 9/2005 | Breece et al. |
| 2005/0232929 A1 | 10/2005 | Kadkhodayan et al. |
| 2005/0272128 A1 | 12/2005 | Umana et al. |
| 2006/0062793 A1 | 3/2006 | Webb et al. |
| 2006/0088539 A1 | 4/2006 | Bander |
| 2006/0159689 A1 | 7/2006 | Chiang et al. |
| 2006/0234226 A1 | 10/2006 | Fahner et al. |
| 2006/0234271 A1 | 10/2006 | Su |

(56) References Cited

U.S. PATENT DOCUMENTS

| | | |
|---|---|---|
| 2006/0269540 A1 | 11/2006 | Robert et al. |
| 2006/0275312 A1 | 12/2006 | Chua et al. |
| 2007/0059306 A1 | 3/2007 | Grosmaire |
| 2007/0134243 A1 | 6/2007 | Gazzard et al. |
| 2007/0212331 A1 | 9/2007 | Baldassare et al. |
| 2007/0243950 A1 | 10/2007 | Billings |
| 2007/0253950 A1 | 11/2007 | Jacobsen |
| 2007/0286858 A1 | 12/2007 | Clancy |
| 2008/0152586 A1 | 6/2008 | Hudson et al. |
| 2008/0171040 A1 | 7/2008 | Ebens et al. |
| 2008/0206192 A1 | 8/2008 | Moller et al. |
| 2008/0213256 A1 | 9/2008 | Kufer et al. |
| 2008/0213921 A1 | 9/2008 | Robertson et al. |
| 2008/0227736 A1 | 9/2008 | Chen et al. |
| 2008/0267872 A1 | 10/2008 | Raitano et al. |
| 2008/0279850 A1 | 11/2008 | Brady et al. |
| 2008/0286284 A1* | 11/2008 | Maddon et al. ............ 424/155.1 |
| 2008/0305105 A1 | 12/2008 | Kufer et al. |
| 2008/0305476 A1 | 12/2008 | Robertson et al. |
| 2009/0004109 A1 | 1/2009 | Jacobovits et al. |
| 2009/0022738 A1 | 1/2009 | Hofmeister et al. |
| 2009/0041758 A1 | 2/2009 | Glaser |
| 2009/0041791 A1 | 2/2009 | Feng |
| 2009/0053223 A1 | 2/2009 | Hoffmann et al. |
| 2009/0099344 A1 | 4/2009 | Fahrner et al. |
| 2009/0136475 A1 | 5/2009 | Barth |
| 2009/0155290 A1 | 6/2009 | Carroll et al. |
| 2009/0202548 A1 | 8/2009 | Gudas |
| 2009/0214539 A1 | 8/2009 | Grosmaire |
| 2009/0226465 A1 | 9/2009 | Jackson |
| 2009/0238755 A1 | 9/2009 | Bander |
| 2009/0252729 A1 | 10/2009 | Farrington et al. |
| 2009/0272169 A1 | 11/2009 | Pan |
| 2009/0275081 A1 | 11/2009 | Barat et al. |
| 2009/0280120 A1 | 11/2009 | Bander et al. |
| 2009/0286258 A1 | 11/2009 | Kaur et al. |
| 2009/0311181 A1 | 12/2009 | Wu et al. |
| 2010/0003766 A1 | 1/2010 | Eigenbrot et al. |
| 2010/0034837 A1 | 2/2010 | Beria et al. |
| 2010/0047239 A1 | 2/2010 | Wu et al. |
| 2010/0058803 A1 | 3/2010 | Ransbarger |
| 2010/0069616 A1 | 3/2010 | Wu et al. |
| 2010/0111856 A1 | 5/2010 | Gill et al. |
| 2010/0135900 A1 | 6/2010 | Cerveny |
| 2010/0184046 A1 | 7/2010 | Klass et al. |
| 2010/0189651 A1 | 7/2010 | Stagliano |
| 2010/0215581 A1 | 8/2010 | Hoffmann |
| 2010/0255479 A1 | 10/2010 | Mikolajczyk et al. |
| 2010/0266491 A1 | 10/2010 | Farokhzad et al. |
| 2010/0267933 A1 | 10/2010 | Wilson |
| 2010/0278919 A1 | 11/2010 | Denes et al. |
| 2010/0297004 A1 | 11/2010 | Wu et al. |
| 2010/0303715 A1 | 12/2010 | Israeli |
| 2010/0303814 A1 | 12/2010 | Cizeau et al. |
| 2010/0303821 A1 | 12/2010 | Ashman |
| 2010/0310452 A1 | 12/2010 | Israeli |
| 2010/0310584 A1 | 12/2010 | Carroll et al. |
| 2011/0006466 A1 | 1/2011 | Ichikawa |
| 2011/0009001 A1 | 1/2011 | Chen |
| 2011/0020327 A1 | 1/2011 | Moya et al. |
| 2011/0069019 A1 | 3/2011 | Carpendale et al. |
| 2011/0076287 A1 | 3/2011 | Cohen et al. |
| 2011/0081345 A1 | 4/2011 | Moore |
| 2011/0086050 A1 | 4/2011 | Presta |
| 2011/0104059 A1 | 5/2011 | St. Croix et al. |
| 2011/0110852 A1 | 5/2011 | Miller et al. |
| 2011/0117023 A1 | 5/2011 | Yamauchi |
| 2011/0123532 A1 | 5/2011 | Gurney et al. |
| 2011/0137017 A1 | 6/2011 | Eigenbrot et al. |
| 2011/0207155 A1 | 8/2011 | Pengo et al. |
| 2011/0227023 A1 | 9/2011 | Bethune et al. |
| 2011/0262968 A1 | 10/2011 | Gudas |
| 2011/0268656 A1 | 11/2011 | Ho |
| 2012/0144110 A1 | 6/2012 | Smith |
| 2012/0283418 A1 | 11/2012 | Wu et al. |

FOREIGN PATENT DOCUMENTS

| | | |
|---|---|---|
| EP | 1 005 494 | 3/1997 |
| EP | 1 550 729 | 7/2005 |
| EP | 1629011 | 3/2006 |
| EP | 1 997 514 | 12/2008 |
| EP | 2226394 | 9/2010 |
| EP | 2260858 | 12/2010 |
| JP | 2003-504414 | 2/2003 |
| WO | 98/52976 | 11/1988 |
| WO | WO 1991/09967 | 7/1991 |
| WO | WO 1993/015199 | 8/1993 |
| WO | WO 1994/09820 | 5/1994 |
| WO | WO 1996/08570 | 3/1996 |
| WO | WO 1996/26272 | 8/1996 |
| WO | WO 97/35616 | 10/1997 |
| WO | 99/47554 | 9/1999 |
| WO | WO 1999/056779 A1 | 11/1999 |
| WO | 2000/02587 A1 | 1/2000 |
| WO | WO 2000/014234 A1 | 3/2000 |
| WO | 00/34317 | 6/2000 |
| WO | WO 01/05427 A1 | 1/2001 |
| WO | WO 2001/009303 A2 | 2/2001 |
| WO | 2001/039798 A1 | 6/2001 |
| WO | WO 2001/082963 A2 | 11/2001 |
| WO | WO 2002/022680 | 3/2002 |
| WO | 02/46448 A2 | 6/2002 |
| WO | 02/098897 | 12/2002 |
| WO | 03/034903 | 5/2003 |
| WO | WO 03/038098 | 5/2003 |
| WO | 2004/098535 A2 | 11/2004 |
| WO | WO 2005/026334 A2 | 3/2005 |
| WO | WO 2005/043165 A2 | 5/2005 |
| WO | WO 2005/061547 A2 | 7/2005 |
| WO | WO 2005/068616 | 7/2005 |
| WO | 2006/110745 A2 | 10/2006 |
| WO | 2006/125481 A1 | 11/2006 |
| WO | WO 2007/064345 A2 | 6/2007 |
| WO | WO 2007/109321 | 9/2007 |
| WO | WO 2007/137117 A2 | 11/2007 |
| WO | WO 2009/017823 | 2/2009 |
| WO | WO 2009/032949 | 3/2009 |
| WO | WO 2009/039854 A2 | 4/2009 |
| WO | WO 2009/076099 A1 | 6/2009 |
| WO | WO 2009/082443 A2 | 7/2009 |
| WO | WO 2009/097128 | 8/2009 |
| WO | WO 2010/037395 A2 | 4/2010 |
| WO | 2010/096486 A1 | 8/2010 |
| WO | WO 2010/102195 A2 | 9/2010 |
| WO | WO 2011/000054 | 1/2011 |
| WO | WO 2011/056983 A1 | 5/2011 |
| WO | WO 2011/069019 | 6/2011 |
| WO | WO 2011/075786 | 6/2011 |
| WO | WO 2011/090762 A1 | 7/2011 |
| WO | WO 2011/109440 A1 | 9/2011 |

OTHER PUBLICATIONS

Shariat et al, Rev. Urol., 2003, vol. 5, No. 1, pp. 54-58.*
Milowsky et al (Journal of Clinical Oncology, vol. 25, No. 5, pp. 540-547) . (Year: 2007).*
De Matos et al, Clinics, vol. 61, No. 5, pp. 417-424. (Year: 2006).*
Sanna, V., et al., "Development of Polymeric Microbubbles Targeted to Prostate-Specific Membrane Antigen as Prototype of Novel Ultrasound Contrast Agents," Mol. Pharmaceutics, vol. 8, 2011, pp. 748-757.
Scott T. et al., "Phase I Biodistribution Study of Ley Targeting Immunoconjugate in Advanced Epithelial Cancers," ASCO Proceedings, Abstract, 2008.
Shi, C., et al., "Visualizing Human Prostate Cancer Cells in Mouse Skeleton Using Bioconjugated Near-Infrared Fluorescent Quantum Dots," Urology, 2009, pp. 1-6.
Silver D.A. et al., "Prostate-Specific Membrane Antigen Expression in Normal and Malignant Human Tissues1," Clin Can Res., vol. 3: 1997, pp. 81-85.
Stahli, C. et al., "[20] Distinction of Epitopes by Monoclonal Antibodies," Methods in Enzymology, vol. 92, 1983, 242-253.

(56) References Cited

OTHER PUBLICATIONS

Stollman, T.H., et al., "New Targeted Probes for Radioimaging of Angiogenesis," Methods, vol. 48, 2009, pp. 188-192.
Sweat, S.D. et al., "Prostate-Specific Membrane Antigen Expression is Greatest in Prostate Adenocarcinoma and Lymph Node Metastases," Urology vol. 52: 1998, pp. 637-640.
Tomlinson, I. M. et al., "The Repertoire of Human Germline VH Sequences Reveals about Fifty Groups of VH Segments with Different Hypervariable Loops," J. Mol. Biol., vol. 227, 1992, pp. 776-798.
Vallabhajosula et al., "Prediction of Myelotoxicity Gased on Bone Marrow Radiation-Absorbed Dose: Radioimmunotherapy Studies Using 90Y- and 177Lu-Labeled J591 Antibodies Specific for Prostate-Specific Membrane Antigen," The Journal of Nuclear Medicine, vol. 46: 2005, pp. 850-858.
Ward, ES., et al., "Binding Activities of a Repertoire of Single Immunoglobulin Variable Domains Secreted from *Escherichia coli*," Nature vol. 341, 1989, pp. 544-546.
Wright, G.L. et al., "Expression of Prostate-Specific Membrane Antigen in Normal, Benign, and Malignant Prostate Tissues," Urol. Oncol. vol. 1, 1995, pp. 18-28.
Wright, G.L., et al., Upregulation of Prostate-Specific Membrane Antigen After Androgen-Deprivation Therapy. Urology 48: 1996, pp. 326-334.
Alt, K., et al., "High-Resolution Animal PET Imaging of Prostate Cancer Xenografts with Three Different 64 Cu-Labeled Antibodies Against Native Cell-Adherent PSMA," The Prostate, 2010, pp. 1-9.
Ananias, H. J. K. et al., "Expression of the Gastrin-Releasing Peptide Receptor, the Prostate Stem Cell Antigen and the Prostate-Specific Membrane Antigen in Lymph Node and Bone Metastases of Prostate Cancer," The Prostate vol. 69: 2009, pp. 1101-1108.
Bander N. H. et al., "Targeting Metastatic Prostate Cancer with Radiolabeled Momoclonal Antibody J591 to the ExtraCellular Domain of Prostate Specific Membrane Antigen," The Journal of Urology, vol. 170: 2003, pp. 1717-1721.
Bander N.H. et al., "Phase I Trial of 177 Lutetium-Labeled J591, a Monoclonal Antibody to Prostate-Specific Membrane Antigen, in Patients with Androgen-Independent Prostate Cancer," J. Clin. Oncol., vol. 23, No. 21, 2005, pp. 4591-4601.
Banerjee, S. R., et al., "68Ga-Labeled Inhibitors of Prostate-Specific Membrane Antigen (PSMA) for Imaging Prostate Cancer," J. Med. Chem., vol. 53, 2010, pp. 5333-5341.
Banerjee, S. R., et al., "Synthesis and Evaluation of Technetium-99m- and Rhenium-Labeled Inhibitors of the Prostate-Specific Membrane Antigen (PSMA)," J. Med. Chem., vol. 51, 2008, pp. 4504-4517.
Belanger L. et al., "Enzyme-Linked Immunoassay for Alpha-Fetoprotein by Competitive and Sandwich Procedures," Clin. Chim. Acta., vol. 48, 1973, pp. 15-18.
Bird, R. E. et al., "Single-Chain Antigen-Binding Proteins," Science, vol. 242: 1988, pp. 423-426.
Bostwick, D.G., et al., Prostate Specific Membrane Antigen Expression in Prostatic Intraepithelial Neoplasia and Adenocarcinoma, Cancer, vol. 82:1998, pp. 2256-2261.
Chang S.S. et al., "Comparison of Anti-Prostate-Specific Membrane Antigen Antibodies and Other Immunomarkers in Metastatic Prostate Carcinoma," Urology, vol. 57; 2001, pp. 1179-1183.
Chang S.S. et al., "Prostate-Specific Membrane Antigen is Produced in Tumor-Associated Neovasculature1," Clinical Cancer Res., vol. 5 No. 10, 1999, pp. 2674-2681.
Chang, S.S. et al., "Five different Anti-Prostate-Specific Membrane Antigen (PSMA) Antibodies Confirm PSMA Expression in Tumor-Associated Neovasculature1," Cancer Res., vol. 59, 1999, pp. 3192-3198.
Chen, Y., et al., "Radiohalogenated Prostate-Specific Membrane Antigen (PSMA)-Based Ureas as Imaging Agents for Prostate Cancer," J. Med. Chem. vol. 51, 2008, pp. 7933-7943.
Chen, Y., et al., "A Low Molecular Weight PSMA-Based Fluorescent Imaging Agent for Cancer," Biochem. Biophys. Res. Commun. 2009, pp. 1-6.

Cheung R. C. et al., "Epitope-Specific Antibody Response to the Surface Antigen of Duck Hepatitis B Virus in Infected Ducks," Virology vol. 176: 1990 pp. 546-552.
Chothia, C. et al. "Canonical Structures for the Hypervariable Regions of Immunoglobulins," J. Mol. Biol. vol. 196, 1987, pp. 901-917.
Chothia, C. et al., "Structural Repertoire of the Human VH Segments," J. Mol. Bio. vol. 227, 1992, pp. 799-817.
Cook, G. P. et al., "The Human Immunoglobulin VH Repertoire," Immunology Today, vol. 16, No. 5, 1995, pp. 237-242.
Coombes R.C. et al., "Prediction of Endocrine Response in Breast Cancer by Immunocytochemical Detection of Oestrogen Receptor in Fine-Needle Aspirates," The Lancent, 1987, pp. 701-703.
International Preliminary Report on Patentability for International App. No. PCT/US2010/024475, dated Aug. 23, 2011 (11 pages).
International Search Report for International Application No. PCT/US2010/024475, dated Aug. 3, 2010 (4 pages).
Eisenberger M. A., et al., "Bilateral Orchiectomy With or Without Flutamide for Metastatic Prostate Cancer," NEJM vol. 339, No. 15, 1998, pp. 1036-1042.
Elsässer-Beile, U., et al., "PET Imaging of Prostate Cancer Xenografts with a Highly Specific Antibody Against the Prostate-Specific Membrane Antigen," The Journal of Nuclear Medicine, vol. 50, No. 4, 2009, pp. 606-611.
Evans, M.J. et al., "Noninvasive Measurement of Androgen Receptor Signaling with a Positron-Emitting Radiopharmaceutical that Targets Prostate-Specific Membrane Antigen," PNAS, 2011, pp. 1-5.
Foss, C.A., et al., Radiolabeled Small-Molecule Ligands for Prostate-Specific Membrane Antigen: In vivo Imaging in Experimental Models of Prostate Cancer, Clin. Cancer Res. vol. 11, No. 11, 2005, pp. 4022-4028.
Haffner, M et al., "Prostate-Specific Membrane Antigen Expression in the Neovasculature of Gastric and Colorectal Cancers," Human Pathology., vol. 40, 2009, pp. 1754-1761.
Hillier, S.M., et al., "123I-MIP-1072, a Small-Molecule Inhibitor of Prostate-Specific Membrane Antigen, Is Effective at Monitoring Tumor Response to Taxane Therapy," J. Nucl. Med., vol. 52, 2011, pp. 1087-1093.
Hillier, S.M., et al., "Preclinical Evaluation of Novel Glutamate-Urea-Lysine Analogues that Target Prostate-Specific Membrane Antigen as Molecular Imaging Pharmaceuticals for Prostate Cancer," Cancer Res., vol. 69. No. 17, 2009, pp. 6932-6940.
Holland, J.P., et al., "89Zr-DFO-J591 for ImmunoPET of Prostate-Specific Membrane Antigen Expression in Vivo," J Nucl Med., vol. 51, 2010, pp. 1293-1300.
Horoszewicz, JS, et al., "Monoclonal Antibodies to a New Antigenic Marker in Epithelial Prostatic Cells and Serum of Prostatic Cancer Patients," Anticancer Res. vol. 7, 1987, pp. 927-936.
Huston, J.S., et al. "Protein Engineering of Antibody Binding Sites: Recovery of Specific Activivty in an Anti-Digoxin Single-Chain Fv Analogue Produced in *Escherichia coli*," Proc. Natl. Acad. Sci. USA vol. 85: 1988, pp. 5879-5883.
Hynecek et al., "177Lu-J591 Monocolonal Antibody (Lu-J591) Therapy in Metastatic Castrate-Resistant Prostate Cancer (metCRPC): Correlation of Antibody-Tumor Targeting and Treatment Response," The Journal of Nuclear Medicine, vol. 49 (Sup. 1): 2008, pp. 144-145.
Kim, K.J., et al., "Epitopes on the S1 Subunit of Pertussis Toxin Recognized by Monoclonal Antibodies," Infect. Immun. vol. 57:1989, pp. 944-950.
Kirkland, T.N. et al., "Analysis of the Fine Specificity and Cross-Reactivity of Monoclonal Anti-Lipid a Antibodies1," J. Immunoi. vol. 137: 1986, pp. 3614-3619.
Kularante, S.A., et al., "Design, Synthesis, and Pre-Clinical Evaluation of Prostate-Specific Membrane Antigen (PSMA)-Targeted 99mTC-Radioimaging Agents," Molecular Pharmaceutics, 2009, pp. 1-28.
Kularante, S.A., et al., "Prostate-Specific Membrane Antigen (PSMA)-Targeted Imaging and Therapy of Prostate Cancer Using a PSMA Inhibitor as a Homing Ligand," Molecular Pharmaceutics, 2009, pp. 1-25.
Lapi, S.E., et al., "Assessment of an 18F-Labeled Phosphoramidate Peptidomimetic as a new Prostate-Specific Membrane Antigen-

(56) References Cited

OTHER PUBLICATIONS

Targeted Imaging Agent for Prostate Cancer," Journal of Nuclear Medicine, Vo. 50, No. 12, 2009, pp. 2042-2048.
Liu, H. et al., Monoclonal Antibodies to the Extracellular Domain of Prostate-Specific Membrane Antigen Also React with Tumor Vascular Endothelium, Cancer Res., vol. 57, No. 17: 1997, pp. 3629-3634.
Mannweiler, S, et al., "Heterogeneity of Prostate-Specific Membrane Antigen (PSMA) Expression in Prostate Carcinoma with Distant Metastasis," Pathol. Oncol. Res., vol. 15, 2009, pp. 167-172.
Maresca, K.P., et al., "A Series of Halogenated Heterodimeric Inhibitors of Prostae Specific Membrane Antigen (PSMA) as Radiolabeled Probes for Targeting Prostate Cancer," J. Med. Chem., vol. 52, 2009, pp. 347-357.
Mease, R.C., et al., "N-[N-[(S)—1,3-Dicarboxypropyl]Carbamoy7l]-4-[18F] Fluorobenzyl-L-Cysteine, [18F]DCFBC: A New Imaging Probe for Prostate Cancer," Clin Cancer Res., vol. 14 No. 10,. 2008, pp. 3036-3043.
Milowsky M.I. et al., "Phase I Trial of Yttruim-90-Labeled Anti-Prostate-Specific Membrane Antigen Monoclonal Antibody J591 for Androgen-Independent Prostate Cancer," J. Clin. Onc., vol. 22, No. 13, 2004 pp. 2522-2531.
Misra, P., et al., "Production of Multimeric Prostate-Specific Membrane Antigen Small-Molecule Radiotracers Using a Solid-Phase 99mTC Preloading Strategy," J. Nucl. Med., vol. 48, 2007, pp. 1379-1389.
Moldenhauer et al., "Identity of HML-1 Antigen on Intestinal Intraepithelial T Cells and of B-Iy7 Antigen on Hairy Cell Leukaemia," Scand. J. Immunol. vol. 32, 1990, pp. 77-82.
Morel, G.A. et al., "Monoclonal Antibodies to Bovine Serum Albumin: Affinity and Specificity Determinations," Mol. Immunoi. vol. 25, No. 1, 1988; pp. 7-15.
Morris, M. et al., "Phase I Evaluation of J591 as a Vascular Targeting Agent in Progressive Solid Tumors," Clin. Can. Res.; vol. 13: 2007 pp. 2707-2713.
Nakajima, T. et al., "Targeted, Activatable, In Vivo Fluorescence Imaging of Prostate-specific Membrane Antigen (PSMA) Positive Tumors Using the Quenched Humanized J591 Anmtibody-Indocyanine Green (ICG) Conuugate," Bioconjugate Chem., 2011, pp. A-F.
O'Dorisio et al., "Combining Anatomic and Molecularly Targeted Imaging in the Diagnosis and Surveillance of Embryonal Tumors of the Nervous and Endocrine Systems in Children," Cancer Metastasis Rev, 2008; vol. 27: pp. 665-677.
Pantaleo et al., "Experimental Results and Related Clinical Implications of PET Detection of Epidermal Growth Factor Receptor (EGFr) in Cancer," Annals of Oncology, vol. 20: 2009; 213-226.
Ross, JS, et al., "Correlation of Primary Tumor Prostate-Specific Membrane Antigen Expression with Disease Recurrence in Prostate Cancer," Clin Can Res., vol. 9: 2003, pp. 6357-6362.
U.S. Appl. No. 08/621,399.
U.S Appl. No. 12/788,477, filed May 27, 2010, Wu et al.
Adams et al., "Highly specific in vivo tumor targeting by monovalent and divalent forms of 741F8 anti-c-erbB-2 single-chain Fv," Cancer Res., Sep. 1, 1993, pp. 4026-4034, vol. 53, No. 17.
Additional Consent Form for Cornell Clinical Investigation by the New York Hospital-Cornell Medical Center.
Albrecht et al., "Development of anti-MUC1 di-scFvs for molecular targeting of epithelial cancers, such as breast and prostate cancers," Dec. 2007, pp. 304-313, vol. 51, No. 4.
Alvarez et al., "Intraperitoneal Radioimmunotherapy of Ovarian Cancer with Lu-CC49: A Phase I/II Study," *Gynecologic Oncology*, 65(1):94:101 Apr. 1997.
Atwell et al., "scFv multimers of the anti-neuranminidase antibody NC10: length of the linker between $V_H$ and $V_L$ domains dictates precisely the transition between diabodies and triabodies," Protein Engineering, Jul. 1999, vol. 12, No. 7, pp. 597-604.
Bander, Neil, H., "Antibody Treatment of Prostate Cancer," CapCure Board Presentation, 18 pages, Nov. 11, 1999.

Barat et al., "Cys-diabody quantum dot conjugates (immunoQdots) for cancer marker detection," Bioconjug. Chem., Aug. 19, 2009, pp. 1474-1781, vol. 20, No. 8.
Bendig, M.M., "Humanization of Rodent Monoclonal Antibodies by CDR Grafting," Methods: A Companion to Methods in Enzymology, 8:83-93, 1995.
Bernard et al., "A Unique Epitope on the CD2 Molecule Defined by the Monoclonal Antibody 9-1: Epitope-Specific Modulation of the E-Rosette Receptor and Effects on T-Cell Functions," *Human Immunology*. 17: 388-405, 1986.
Boyer et al., "Relative Cytotoxic Activity of Immunotoxins Reative Reactive with Different Epitopes on the Extracellular Domain of the c-erB-2 (Her-2/neu) *Gene Product,*" *Int. J. Cancer*, 82:525-531, 1999.
Carmichael et al., "The crystal structure of an anti-CEA scFv diabody assembled from T84.66 scFvs in V(L)-to-V(H) orientation: Implications for diabody flexibility," J. Mol. Biol., Feb. 14, 2003, pp. 341-351, vol. 326, No. 2.
Casset, F., et al., "A peptide mimetic of an anti-CD4 monoclonal antibody by rational design," Biochemical and Biophysical Research Communications 307, 2003, pp. 198-205.
City of Hope National Medical Center, "Anti-CEA antibody T84.66 humanized," Medical Imaging Law Weekly, copyright 2004, http://www.newsrx.com/newsletters/Medical-Imaging-Law-Weekly; dated for online publication Nov. 27, 2004.
Colman, P.M., "Effects on amino acid sequence changes on antibody-antigen interactions," *Research in Immunology*, 145:33-36, 1994.
Common Toxicity Criteria, Version 2.0, National Cancer Insttitute, Cancer Therapy Evaluation Program, Jun. 1, 1999.
Communication pursuant to Rules 70(2) and 70a(2) EPC dated Dec. 28, 2010, received in EP Appl. No. 08799192.3, 11 pages.
De Pascalis et al., "Grafting of "Abbreviated" Complementarity-Determining Regions Containing Specificity-Determining Residues Essential for Ligand Contact to Engineer a Less Immunogenic Humanized Monoclonal Antibody," J. Immunol. 169(6): 3076-3084, 2002.
Desantes et al., "Radiolabeled Antibody Targeting of the HER-2/neu Oncoprotein," *Cancer Research* 52:1916-1923, Apr. 1, 1992.
Desplancq et al., "Multimerization behaviour of single chain Fv variants for the tumour-binding antibody B72.3," Protein Engineering, Aug. 1994, vol. 7, No. 8, pp. 1027-1033.
Dillman, *Annals of Internal Medicine*, 111:592-603, 1989.
File History, U.S. Appl. No. 08/256,156, filed Jun. 24, 1994.
File History, U.S. Appl. No. 08/838,682, filed Apr. 9, 1997.
File History, U.S. Appl. No. 08/895,914, filed Jul. 17, 1997.
File History, U.S. Appl. No. 09/357,704, filed Jul. 20, 1999.
File History, U.S. Appl. No. 09/357,707, filed Jul. 20, 1999.
File History, U.S. Appl. No. 09/357,708, filed Jul. 20, 1999.
File History, U.S. Appl. No. 09/357,709, filed Jul. 20, 1999.
File History, U.S. Appl. No. 09/929,546, filed Aug. 13, 2001.
File History, U.S. Appl. No. 10/160,505, filed May 30, 2002.
File History, U.S. Appl. No. 10/449,379, filed May 30, 2003.
File History, U.S. Appl. No. 11/218,813, filed Sep. 2, 2005.
File History, U.S. Appl. No. 11/219,563, filed Sep. 2, 2005.
File History, U.S. Appl. No. 12/371,399, filed Feb. 13, 2009.
File History, U.S. Appl. No. 10/690,990, filed Oct. 23, 2003.
File History, U.S. Appl. No. 12/293,860, filed Sep. 22, 2008.
File History, U.S. Appl. No. 12/363,678, filed Jan. 30, 2009.
File History, U.S. Appl. No. 12/537,145, filed Aug. 6, 2009.
File History, U.S. Appl. No. 12/676,348, filed Aug. 5, 2010.
File History, U.S. Appl. No. 12/788,477, filed May 27, 2010.
File History, U.S. Appl. No. 12/959,340, filed Dec. 2, 2010.
File History, U.S. Appl. No. 13/554,306, filed Jul. 20, 2012.
Fitzgerald et al., "Improved Tumor Targeting by Disulphide Stabilized Diabodies Expressed in Pichia Pastoris." *Protein Engineering* 10.10 (1997): 1221-1225.
Forni et al., "Immunoprevention of Cancer: Is the Time Ripe?" *Cancer Research*, 60; 2571-2575, 2000.
George et al., "Radiometal labeling of recombinant proteins by a genetically engineered minimal chelation site: technetium-99m coordination by single-chain Fv antibody fusion proteins through a C-terminal cysteinyl peptide," Proc. Natl. Acad. Sci. USA, Aug. 1995, vol. 92, No. 18, pp. 8358-8362.

(56) References Cited

OTHER PUBLICATIONS

George et al., "Differential Effects on Anti-β₂-Glycoprotein I Antibodies on Endothelial Cells and on the Manifestations of Experimental Antiphospholipid Syndrom." *Circulation*, 97: 900-906, 1998.
Glockshuber et al., "A comparison of strategies to stabilize immunoglobulin Fv-fragments," Biochemistry, 1990, pp. 1362-1367, vol. 29, No. 6.
Greenspan et al., "Defining epitopes: It's not as easy as it seems," *Nature Biotechnology*, 7:936-937, 1999.
Gu et al., "Biological activity and microPET imaging properties of chimeric and humanized anit-prostate stem cell antigen (PSCA) antibodies," Proc Amer Assoc Cancer Res., 2005, vol. 46, Abstract #696 [Retrieved on May 14, 2012], URL: http://aacrmeetingabstracts.org/cgi/content/abstract/2005/1/164-b.
Gura, T., "Systems for Identifying New Drugs are Often Faulty," *Science*, 278:1041-1042, Nov. 7, 1997.
Güssow et al., "Humanization of Monoclonal Antibodies," *Methods in Enzyumology*, 203:99-121 1991.
Henry et al., "A Prostate-Specific Membrane Antigen-Targeted Monoclonal Anti-body Chemotherapeutic Conjugate Designed for the Treatment of Prostate Cancer," *Cancer Research.*, 64: 7995-8001, Nov. 1, 2004.
Hinman et al., "Preparation and Characterization of Monoclonal Antibody Conjugates of the Calicheamicins: A Novel and Potent Family of Antitumor Antibiotics," *Cancer Research*, 53: 3335-23342, 1993.
Hollinger et al., ""Diabodies": Small bivalent and bispecific antibody fragments," Proc. Natl. Acad. Sci. USA, Jul. 1993, pp. 6444-6448, vol. 90.
Holm et al., "Functional mapping and single chain construction of the anti-Cytokeratin 8 monoclonal antibody TS1," *Molecular Immunology.*, 44 (6): 1075-1084, 2007.
Holmes et. al., "PSMA Specific Antibodies and Their Diagnostic and Therapeutic Use," Expert Opinion on Investigational Drugs, 10 (3); 544-519 (2001).
Hopp et al., "A Computer Program for Predicting Protein Antigenic Determinants," Molecular Immunology, 1983, pp. 483-489, vol. 20 (4).
Hu et al., "Minibody: A Novel Engineered Anti-carcinoembryonic Antigen Antibody Fragment (Single-Chain $F_V$-$C_H^3$) Which Exhibits Rapid, High-Level Targeting of Xenografts." *Cancer Research* 56 (Jul. 1, 1996): 3055-3061.
International Search Report & Written Opinion dated Mar. 21, 2012 for International Application No. PCT/US2010/058803, filed Dec. 2, 2010.
International Search Report and Written Opinion dated Apr. 22, 2009, from Int'l Appl. No. PCT/US2008/075291 (WO 2009/032949).
International Search Report and Written Opinion dated Apr. 23, 2008, from Int'l Appl. No. PCT/US2007/007020 (WO 2007/109321).
Israeli, Ron S. et .la "Molecular Cloning of a Complementary DNA Encoding a Prostate-Specific Membrane Antigen", Cancer Research 53, 227-230, Jan. 15, 1993.
Jain et al., "Vascular and interstitial barriers to delivery of therapeutic agents in tumors," Cancer and Metastasis Reviews 9: pp. 253-266, 1990.
Jain, R.K., "Barriers to Drug Delivery in Solid Tumors," *Scientific American*, pp. 58-65, Jul. 1994.
Jiang et al., "A Novel Peptide Isolated from a Phage Display Peptide Library with Trastuzumab Can Mimic Antigen Epitope of HER-2*," *J. Biol. Chem.*, 280 (6): 4656-4662, Feb. 11, 2005.
Johnson et al., "Effector cell recruitment with novel Fv-based dual-affinity re-targeting protein leads to potent tumor cytolysis and in vivo B-cell depletion," J. Mol. Biol., Jun. 11, 2010, pp. 436-449, vol. 399, No. 3.
Kim et al., "Both the Epitope Specificity and Isotype are Important in the Antitumor Effect of Monoclonal Antibodies Against Her-2/NEU Antigen," *Int. J. Cancer*, 102: 428-434, 2002.

Kim et al., "Anti-CD30 diabody-drug conjugates with potent antitumor activity," Mol. Cancer Ther., Aug. 2008, pp. 2486-2497, vol. 7, No. 8.
Kinoshita et al., "Targeting epitopes in prostate-specific membrane antigen for antibody therapy of prostate cancer," *Prostate Cancer and Prostatic Diseases*, 8: 359-363, 2005.
Kukis et al., "Effect of the extent of chelate substitution on the immunoreactivity and biodistribution of 2IT-BAT-Lym-1 immunoconjugates", *Cancer Research*, vol. 55, pp. 878-884 (Feb. 1, 1995).
Leung et al., "Engineering a Unique Glycosylation Site for Site-Specific Conjugation of Haptens to Antibody Fragments." *The Journal of Immunology* 154 (1995): 5919-5926.
Lewis et al., "An improved method for conjugating monoclonal antibodies with N-Hydroxysulfosuccinimidyl DOTA", *Bioconjugate Chem*, vol. 12, pp. 320-324 (2001).
Lewis et al., "Differential responses of human tumor cell lines to anti-p185$^{HER2}$ monoclonal antibodies," *Cancer Immunol. Immunther.*, 27:255-263, 1993.
Leyton et al., "Humanized radioiodinated minibody for imaging of prostate stem cell antigen-expressing tumors", *Clinical Cancer Research*, vol. 14 No. 22, pp. 7488-7496 (Nov. 15, 2008).
Li et al., "Improved biodistribution and radioimmunoimaging with poly(ethylene glycol)-DOTA-conjugated anti-CEA diabody," Bioconjug. Chem., Jan.-Feb. 2006, pp. 68-76, vol. 17, No. 1.
Li et al., "Reduction of kidney uptake in radiometal labeled peptide linkers conjugated to recombinant antibody fragments, site-specific conjugation of DOTA-peptides to a Cys-diabody," Bioconjugate Chem., 2002, pp. 985-995, vol. 13, No. 5.
Li et al., "Labeling Monoclonal Antibodies with Yttrium and Indium-DOTA Chelates: A Simple and Efficient Method," *Bioconjugate Chemistry*, 5(2): 101-104, 1994.
Liu et al., "Constitutive and antibody-induced internalization of prostate-specific membrane antigen", *Cancer Research*, vol. 58, pp. 4055-4060 (Sep. 1, 1998).
Liu et al., "Eradication of large colon tumor xenografts by targeted delivery of maytansinoids," *Proc. Natl. Acad. Sci. USA*, 93:8618-8623, 1996.
Maccallum et al., *J. Mol. Biol.* 262, 732-745, 1996 Maccallum et al., "Antibody-antigen Interactions: Contact Analysis and Binding Site Topograph," *J Mol. Biol.* 262, 732-745, 1996.
Marty et al., "Production of functionalized single-chain Fv antibody fragments binding to the ED-B domain of the B-isoform of fibronectin in *Pichia pastoris*," Protein Expression and Purification, Feb. 2001, vol. 21, Issue 1, pp. 156-164.
McCartney et al., "Engineering disulfide-linked single-chain Fv dimers [(sFv')2] with improved solution and targeting properties: anti-digoxin 26-10 (sFv')2 and anti-c-erbB-2 741F8 (sFv')2 made by protein folding and bonded through C-terminal cysteinyl peptides." Protein Eng. 8.3 (Mar. 1995):301-14.
McCartney et al., Refolding of single-chain Fv with C-terminal cysteine (sFv); formation of disulfide-bonded homodimers of antic-Af/7B-2 and anti-digoxin sFv', Miami Short Rep., 1993, vol. 3, p. 91.
McDevitt et al., An—Particle Emitting Antibody ([$^{213}$Bi]J591) for Radioimmunotherapy of Prostate Cancer, *Cancer Res.*, 60: 6095-6100, Nov. 1, 2000.
Milowsky et al., "Vascular targeted therapy with anti-prostate-specific membrane antigen monoclonal antibody J591 in advanced solid tumors", Journal of Clinical Oncology, vol. 25 No. 5, pp. 540-547 (Feb. 10, 2007).
Moore et al., "Application of dual affinity retargeting molecules to achieve optimal redirected T-cell killing B-cell lymphoma," Blood, Apr. 28, 2011, pp. 4542-4551, vol. 117, No. 17.
Morris et al., "Pilot trial of unlabeled and indium-111-labeled anti-prostate-specific membrane antigen antibody J591 for castrate metastatic prostate cancer", *Clinical Cancer Research*, vol. 11, pp. 7454-7461 (2005).
Murphy G et. al., "Comparison of prostate Specific Membrane Antigen, and Prostate Specific Antigen Levels in Prostatic Cancer Patients," Anticancer Research 15: pp. 1473-1480, (1995).

(56) References Cited

OTHER PUBLICATIONS

Murphy G P et. al., "Measurement of Prostate-Specific Membrane Antigen in the Serum With a New Antibody," The Prostate 28: pp. 266-271, (Apr. 1996).
Murphy G P et. al., "A comparison of prostate specific antigen, prostate specific membrane antigen and LnCaP based ELISA assays in prostatic cancer patients and patients with benign prostatic enlargement" The Prostate 26: pp. 164-168, (1995).
Neumaier et al., "Cloning of the genes for T84.66, and antibody that has a high specificity and affinity for carcinoembryonic antigen, and expression of chimeric human/mouse T84.66 genes in myeloma and Chinese hamster ovary cells," Cancer Research, 1990, vol. 50, pp. 2128-2134.
Notice of Opposition to European Patent Application No. 0668777 filed Jul. 11, 2007 by BZL Biologics LLC.
Notice of Opposition to European Patent Application No. 0956506 filed Dec. 1, 2006 by PSMA Development Company LLC.
Office Action issued in U.S. Appl. No. 12/788,477, filed May 27, 2012 in 22 pages.
Olafsen et al., "Characterization of engineered anti-p185 $^{HER-2}$ (scFv-$C_H3$)$_2$ antibody fragments (minibodies) for tumor targeting", Protein Engineering, Design & Selection, vol. 17 No. 4, pp. 315-323, Oxford University Press (2004).
Olafsen et al., "Covalent disulfide-linked anti-CEA diabody allows site-specific conjugation and radiolabeling for tumor targeting applications," Protein Eng. Des. Sel., Jan. 2004, pp. 21-27, vol. 17, No. 1.
Olafsen et al., "ImmunoPET imaging of B-cell lymphoma using 124I-anti-CD20 scFv dimers (diabodies)," Protein Eng. Des. Sel., Apr. 2010, pp. 243-249, vol. 23, No. 4.
Olafsen et al., "Recombinant anti-CD20 antibody fragments for small-animal PET imaging of B-Cell lymphomas", The Journal of Nuclear Medicine, vol. 50 No. 9, pp. 1500-1508 (Sep. 2009).
Olafsen et al., "Tunable pharmacokinetics: modifying the in vivo half-life of antibodies by directed mutagenesis of the Fc fragment", Nature Protocols, vol. 1 No. 4, pp. 2048-2060 (2006).
Olson et al., "Clinical trials of cancer therapies targeting prostate-specific membrane antigen", Reviews on Recent Clinical Trials, vol. 2, pp. 182-190 (2007).
Panka et al., "Variable region framework differences result in decreased or increased affinity of variant anti-digoxin antibodies," Proc Natl Acad Sci USA, vol. 85 3080-3084, Apr. 1988.
Paul, W.E., "Fundamental Immunology," 3d ed., pp. 242, 292-295 1993.
Persiani S et., al., Cancer Immunol Immunother (1989), 29: pp. 167-170 In vivo antitumor effect of methotrexate conjugated to a monoclonal IgM antibody specific for stage-specific embryonic antigen-1, on MH-15 mouse teratocarcinoma.
Pettersen et al., "CD47 Signals T Cell Death," J. Immunol., 162 (12): 7031-7040, Jun. 15, 1999.
Preliminary Amendment filed on Dec. 21, 2011 in U.S. Appl. No. 12/788,477 (filed May 27, 2012) in 9 pages.
Press et al., "Ricin A-Chain Containing Immunotoxins Directed Against Different Epitopes on the CD2 Molecule Differ in Their Ability to Kill Normal and Malignant T Cells," J. Imunol., 141 (12): 4410-4417, 1998.
Raag et al., "Single-chain Fvs." FASEB J., Jan. 1995, vol. 9, No. 1, pp. 73-80.
Rajasekaran S.A. et. al., Molecular Biology of the Cell, vol. 14, pp. 4835-4845, Dec. 2003 A Novel Cytoplasmic Tail MXXXL Motif Mediates the Internalization of Prostate-specific Membrane Antigen.
Richstone et al., "Eradication of Prostate Cancer Xenografts by Immunoconjugates Targeting the Extracellular Domain of Prostate-Specific Membrane Antigen (PSMA)," Proceedings of the American Society of Clinical Oncology, vol. 19, abstract 1329, May 20, 2000.
Riemer et al., "Matching of trastuzumab (Herceptin®) epitope mimics onto the surface of Her-2/neu-a new jethod of epitope definition," Mol. Immunol., 42: 1121-1124, 2005.
Rudikoff et al., "Singe Amino Acid Substitution Altering Antigen-Binding Specificity," Proc. Natl. Acad. Sci. USA, Mar. 1982, pp. 1979-1983, vol. 79.
Schlom, "Molecular Foundations of Oncology", Chapter 6, pp. 93-134, 1991.
Schulke et. al., "The Homodimer of Prostate-Specific Membrane Antigen is a Functional Target for Cancer Therapy," PNAS, 100 (22), pp. 12590-12595, Oct. 28, 2003.
Shinnick et al., "Peptide-Elicited Protein-Reactive Antibodies in Molecular Biology and Medicine," J. Invest. Dermatol., 83 (1 Suppl.): 112s-115s, Jul. 1984.
Silver D A et. al., "Prostate-specific membrane antigen expression in normal and malignant human tissues," Clinical Cancer Research, vol. 3, pp. 81-85, Jan. 1997.
Sirk et al., "Site-specific, thiol-mediated conjugation of fluorescent probes to cysteine-modified diabodies targeting CD20 or HER2," Dec. 2008, pp. 2527-2534, vol. 19, No. 12.
Slovin, "Targeting novel antigens for prostate cancer treatment: focus on prostate-specific membrane antigen", NIH Public Access: Author Manuscript, Expert Opinon Ther Targets, vol. 9 No. 3, pp. 561-570 (Jun. 2005).
Smith, S., "Technology evaluation: C242-DM1, ImmunoGem, Inc." Current Opinion in Molecular Therapeutics, 3(2):198-203, Apr. 2001.
Stancoviski et al., "Mechanistic aspects of the opposing effects of monoclonal antibodies to the ERBB2 receptor on tumor growth," Proceedings of the National Academy of Science USA, 88: 8691-8695 (1991).
Stimmel et al., "Site-specific conjugation on serine → Cysteine variant monoclonal antibodies," The Journal of Biological Chemistry, Sep. 29, 2000, pp. 30445-30450, vol. 275, No. 39.
Tai et al., "Targeting c-erbB-2 expressing tumors using single-chain Fv monomers and dimers," Cancer Res., Dec. 1, 1995, pp. 5983s-5989s, vol. 55, No. 23 Suppl.
Tazzari P.L. et al., "An immunotoxin containing a rat IgM monoclonal antibody (Campath 1) and saporin 6: effect on T lymphocytes and hemopoietic cells," Cancer Immunol Immunother (1988) 26: pp. 231-236.
Troyer, J.K., et al., "Location of Prostate-Specific Membrane Antigen in the LNCaP Prostate Carcinoma Cell Line," The Prostate 30, 1997, pp. 232-242.
Troyer J K et. al., Detection and characterization of the prostate specific membrane antigen (PSMA) in tissue extracts and body fluids,: Int. J. Cancer: 62, pp. 552-558, (1995).
Troyer J K et. al., Biochemical characterization and mapping of the 7E11C5.3 epitope of the prostate specific membrane antigen, Urol. Oconl., 1995; 1: pp. 29-37, (1995).
U.S. Appl. No. 10/690,990, filed Oct. 23, 2002.
U.S. Appl. No. 12/788,477, filed May 27, 2012.
Urva et al., "Physiologically based pharmacokinetic (PBPK) model for T.84.66, a monoclonal anti-CEA antibody," Am. Assoc. Pharm. Sci. 10 (Supp. 2), 2008, pp. 957.
Usui H. et. al, "Evaluation of Ricin a Chain-Containing Immunotoxins Directed Against Glycolipid and Glycoprotein on Mouse Lymphoma Cells" ., Acta Med Okayama, 1994; 48 (6): pp. 305-309.
Vaidyanathan et al., "Evaluation of an anti-p 185$^{HER2}$ (scFv-$C_H$2-$C_H$2)$_2$ fragment following radioiodination using two different residualizing labels: SGMIB and IB-Mal-D-GEEEK*," Nuclear Medicine and Biology, 2009, pp. 671-680, vol. 36.
Verhaar et al., "Technetium-99m radiolabeling using a phage-derived single-chain Fv with a C-terminal cysteine," The Journal of Nuclear Medicine, May 1996, pp. 868-872, vol. 37, No. 5.
Veri et al., "Therapeutic control of B cell activation via recruitment of Fcgamma receptor IIb (CD32B) inhibitory function with a novel bispecific antibody scaffold." Arthritis Rheum. 62.7 (Jul. 2010): 1933-43.
Weiner, "An Overview of Monoclonal Antibody Therapy of Cancer," Seminars Oncology, vol. 26, No. 4, pp. 41-50, 1999.
Whitlow et al., "Multivalent Fvs: characterization of single-chain Fv oligomers and preparation of a bispecific Fv," Protein Engineering, Aug. 1994, vol. 7, No. 8, pp. 1017-1026.

(56) References Cited

OTHER PUBLICATIONS

Wiedloha A. et. al, "Specific killing of mouse leukemic cells with ricin A-chain immunotoxin,"., Archivum Immunologiae et Therapiae Experimentalis, 1989, 37, pp. 101-113.
Wiels J. et. at., "Properties of immunotoxins against a glycolipid antigen associated with Burkitt's lymphoma," Cancer Research 44, pp. 129-133, Jan. 1984.
Wong et al., "Pilot trial evaluating an $^{123}$I-Labeled 80-Kilodalton engineered anticarcinoembryonic antigen antibody fragment (cT84.66 minibody) in patients with colorectal cancer", *Clinical Cancer Research*, vol. 10, pp. 5014-5021 (Aug. 1, 2004).
Wu et al, "Antibodies for molecular imaging of cancer", *The Cancer Journal*, vol. 14 No. 3, pp. 191-197 (May/Jun. 2008).
Wu et al., "Antibodies and antimatter: The Resurgence of Immuno-PET", *The Journal of Nuclear Medicine*, vol. 50 No. 1, pp. 2-5 (Jan. 2009).
Wu et al., "Anti-carcinoembryonic antigen (CEA) diabody for rapid tumor targeting and imaging," Tumor Targeting, 1999, pp. 47-58, vol. 4.
Wu et al., "Arming antibodies: prospects and challenges for immunoconjugates", *Nature Biotechnology*, vol. 23 No. 9, pp. 1137-1146 (Sep. 2005).
Wu et al., "High-resolution microPET imaging of carcinoembryonic antigen-positive xenografts by using a copper-64-labeled engineered antibody fragment," Proc. Natl. Acad. Sci. USA, 2000, pp. 8495-8500, vol. 97, No. 15.
Wu et al., "Tumor localization of anti-CEA single-chain Fvs: Improved targeting by non-convalent dimmers," Immunotechnology, 1996, pp. 21-36, vol. 2.

Wu et al. "Humanization of a Murine Monoclonal Antibody by Simultaneous Optimization of Framework and CDR Residues," *J. Mol. Biol.*, 294(1): 151-162, Nov. 19, 1999.
Xu et al., "Antibody-Induced Growth Inhibition is Mediated Through Immunochemically and Functionally Distinct Epitopes on the Extracellular Domain of the c-erbB-2 (Her-2/neu) Gene Product," *Int. J. Cancer*, 53: 401-408, 1993.
Yazaki et al., "Mammalian expression and hollow fiber bioreactor production of recombinant anti-CEA diabody and minibody for clinical applications," Journal of Immunological Methods, 2001, pp. 195-208, vol. 253.
Yazaki et al., "Tumor Targeting of Radiometal Labeled Anti-CEA Recombinant T84.66 Diabody and T84.66 Minibody: Comparision to Radioiodinated Fragments." *Bioconjugate Chem.* 12 (2001): 220-228.
You et al., "Expression, purification, and characterization of a two domain carcinoembryonic antigen minigene (N-A3) in pichia pastoris the essential role of the N-domain," Anticancer Research, 1998, pp. 3193-3202, vol. 18.
Brunner, What is the difference between "predictive and prognostic biomarkers"? Can you give some examples? Connection: 18; (2009).
Clark, "Prognostic factors versus predictive factors: Examples from a clinical trial of erlotinib," Molecular Oncology 1: 406-12 (2008).
Gale t al., "Meniscal subluxation: association with osteoarthritis and joint space narrowing", Osteoarthritis and Cartilage, (1999) 7, pp. 526-532.
Reichenbach et al., "Prevalence of Bone Attrition on Knee Radiographs and MRI in a Community-based Cohort", Osteoarthritis Cartilage, (2008) 16(9): pp. 1005-1010.

\* cited by examiner

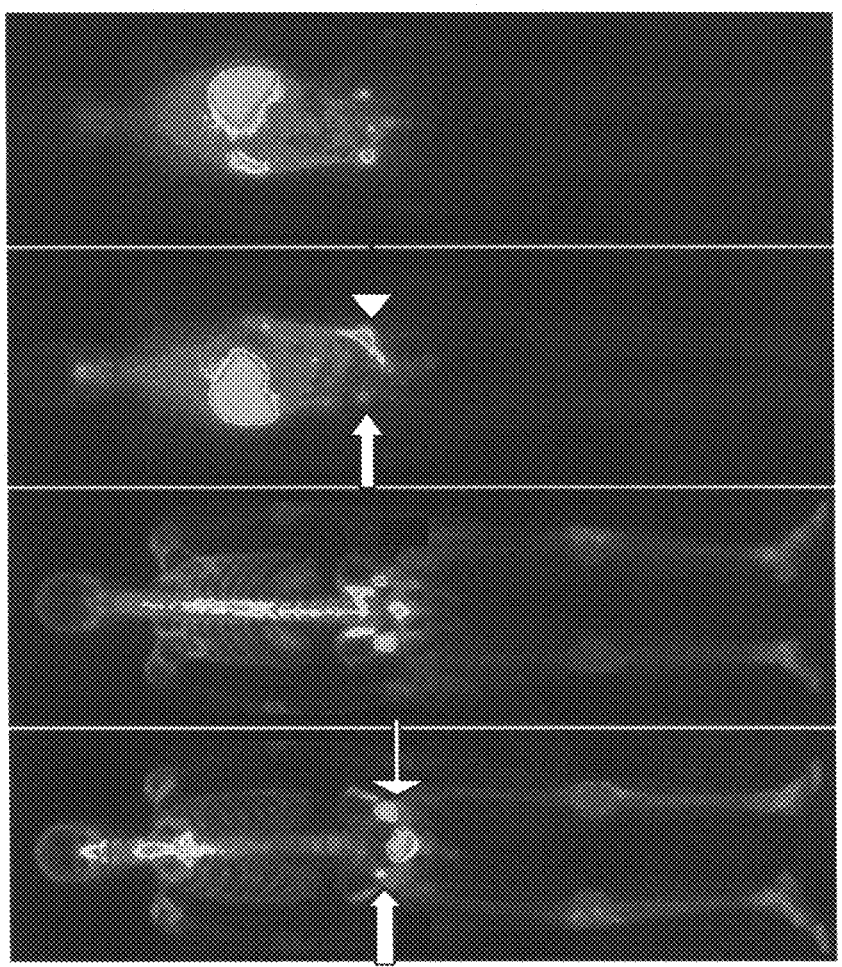

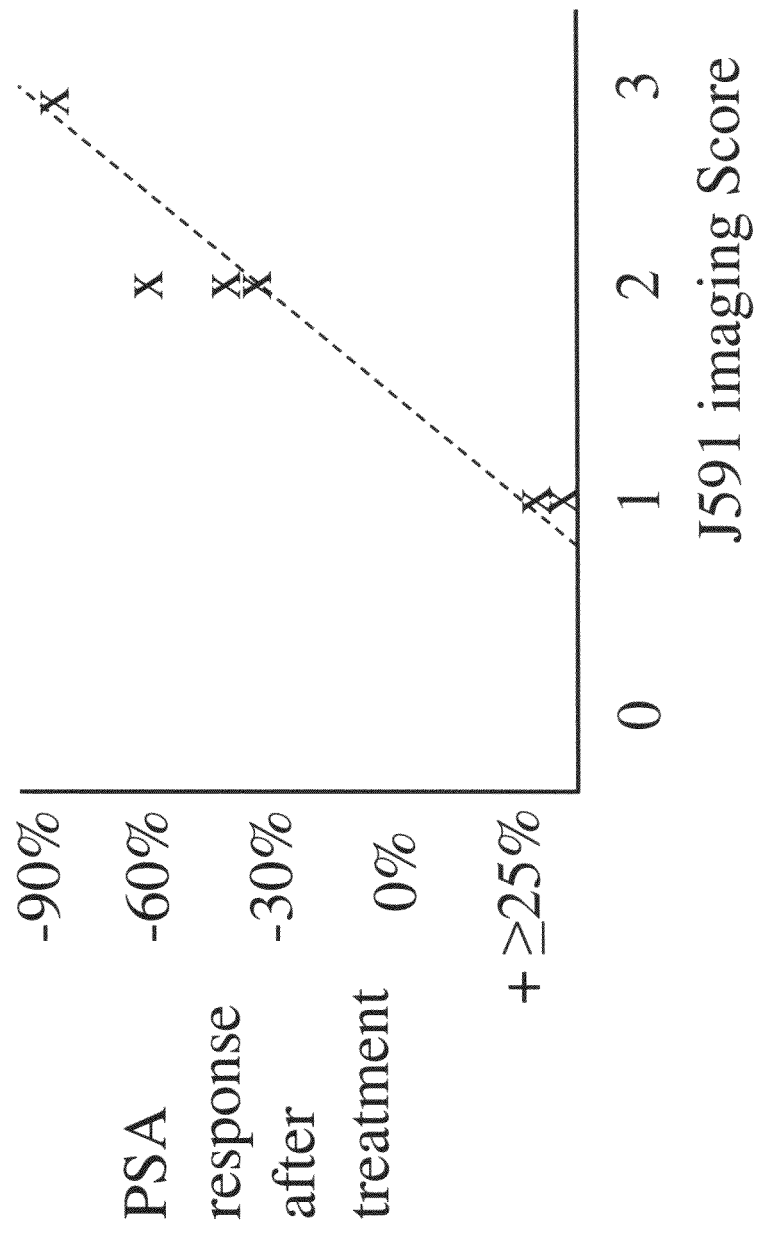

METHODS AND KITS FOR DIAGNOSIS OF CANCER AND PREDICTION OF THERAPEUTIC VALUE

RELATED APPLICATIONS

This application claims the benefit of U.S. Provisional Application No. 61/153,132, filed Feb. 17, 2009, which application is hereby incorporated by reference in its entirety. Reference is also made to the PCT International Application filed in the U.S. Receiving Office on Feb. 17, 2010, under PCT/US10/22475, "Methods and Kits for Diagnosis of Cancer and Prediction of Therapeutic Value" by Bander et al., which also claims priority to U.S. Provisional Application No. 61/153,132, filed Feb. 17, 2009, and which is hereby also incorporated by reference in its entirety.

FIELD OF THE INVENTION

The invention relates generally to methods for identifying and/or selecting a patient for cancer therapy. The invention relates more particularly to using quantitative or semi-quantitative imaging to predict the therapeutic value of various cancer therapies.

BACKGROUND OF THE INVENTION

Prostate cancer is one of the most common causes of cancer deaths in American males. In 2007, approximately 219,000 new cases are expected to be diagnosed as well as 27,000 deaths due to this disease (NCI SEER data; Cancer Facts and Figures, American Cancer Society). There are currently very limited treatment options for prostate cancer patients once the cancer has metastasized (spread beyond the prostate). Systemic therapy is primarily limited to various forms of androgen (male hormone) deprivation. While most patients will demonstrate initial clinical improvement, virtually inevitably, androgen-independent cells develop. Endocrine therapy is thus palliative, not curative. (Eisenberger M. A., et al. (1998) NEJM 339:1036-42). Median overall survival in these patients where androgen-independent cells have developed was 28-52 months from the onset of hormonal treatment (Eisenberger M. A., et al. (1998) supra.). Subsequent to developing androgen-independence, only taxane-based (i.e., docetaxel) chemotherapy has been shown to provide a survival benefit, with a median survival of 19 months. Once patients fail to respond to docetaxel, median survival is 12 months.

Where prostate cancer is localized and the patient's life expectancy is 10 years or more, radical prostatectomy offers the best chance for eradication of the disease. Historically, the drawback of this procedure is that many cancers had spread beyond the boundaries of the operation by the time the cancers were detected. However, the use of prostate-specific antigen (PSA) testing has permitted early detection of prostate cancer. As a result, surgery is less extensive with fewer complications. Patients with bulky, high-grade tumors are less likely to be successfully treated by radical prostatectomy. Radiation therapy has also been widely used as an alternative to radical prostatectomy. Patients generally treated by radiation therapy are those who are older and less healthy and those with higher-grade, more clinically advanced tumors. However, after surgery or radiation therapy, if there are detectable serum PSA concentrations, persistent cancer is indicated. In many cases, PSA concentrations can be reduced by radiation treatment. However, this PSA concentration often increases again within two years signaling disease recurrence.

For treatment of patients with locally advanced disease, hormonal therapy before or following radical prostatectomy or radiation therapy has been utilized. Orchiectomy (removal of the testicles) reduces serum testosterone concentrations, while estrogen treatment has a similar effect.

Prostate Specific Membrane Antigen (PSMA) is present on the cell surface of some normal prostatic epithelial cells, normal renal proximal tubular cells, proximal small bowel and some astrocytes (found in the brain). PSMA is highly upregulated/overexpressed on prostate cancer (Pca) cells. Expression levels of PSMA increase along with prostate cancer progression and higher PSMA levels in early stage Pca predict a higher likelihood of recurrence.

Furthermore, virtually all solid tumors express PSMA in their tumor neo-vasculature whereas normal vascular endothelium is PSMA-negative.

Monoclonal antibodies which recognize PSMA have been developed, including 7E11, which binds to the intracellular domain. (Horoszewicz et al. (1987) Anticancer Res. 7:927-936; U.S. Pat. Nos. 5,162,504; 6,107,090; 6,150,508; and 7,045,605), and other anti-PSMA antibodies that bind the extracellular domain.

Cancer treatments often include administering therapeutic agents that have adverse or otherwise undesirable side effects, including toxicity. Further, the effect of a given treatment on the cancer of an individual patient is variable. In some patients, the given treatment can be highly effective, while in others, it can have little or no effect on the cancer. Furthermore, because of unpredictable and variable treatment outcomes, clinical trials must be very large to reach statistical significance. Large clinical trials can become prohibitively expensive or otherwise impracticable. Therefore, there is a need for improved treatments that mitigate toxicity, improve likelihood of a favorable outcome, and to facilitate clinical trials.

SUMMARY OF THE INVENTION

The invention includes methods and kits for diagnosing and treating cancer. In some aspects, the invention relates to methods of identifying a patient or subject for cancer therapy. The methods comprise providing a first binding agent capable of binding a first molecular target, wherein the presence of the first molecular target cancer-related or indicative of cancer. The presence of the first binding agent can then be assessed in a tissue, cell(s) or bodily fluid. Preferably, the first binding agent comprises a label moiety. In some embodiments, the presence of the first binding agent is assessed by in vivo imaging or the presence of the first binding agent can be assayed in a biological sample obtained from the patient. The presence of the first binding agent may be assessed qualitatively (e.g. visually), semi-quantitatively, or quantitatively. Where appropriate, the methods also include administering to the patient a therapeutic dose of a second binding agent capable of binding a molecular or cellular target.

In some aspects of the invention, the methods include administering a diagnostic dose of a detectably labeled first binding agent to a patient. The detectably labeled first binding agent is capable of binding a molecular target associated with the cancer (e.g., a cancer cell or associated cell such as the neo-vasculature of a solid tumor). Where appropriate, the methods also include administering to the patient a therapeutic dose of a second binding agent capable of binding a molecular or cellular target. The patient or patients are selected for therapy based on a result of administering the diagnostic dose (e.g., a non-invasive, in vivo diagnosis). The results can include, for example, imaging and/or otherwise quantifying a level and/or localization of the first binding agent in the patient. Patients that are not expected to benefit from a particular therapy can thus be identified prior to therapy and spared the therapy and/or directed to an alternative therapy. In one embodiment, the second binding agent may bind to the same target molecule as the first binding agent. Yet in another embodiment, the second binding therapeutic agent may target a different molecule. In some embodiments, the first and second binding agent target molecules that are functionally related. For example, the first and second molecular target may be part of a common pathway.

In some aspects of the invention, the methods for identifying a patient for cancer therapy comprises (i) providing a first binding agent capable of binding a first molecular target, wherein the first molecular target is selected from a pathway related to cancer; (ii) assessing the presence of the first binding agent in a tissue, cells or bodily fluid in a patient; and (iii) selecting a patient for administration of a therapeutic dose of a second binding agent capable of binding a second molecular target, wherein the patient is selected if the first binding agent is present.

In some aspects of the invention, the methods for identifying a patient for cancer therapy comprises (i) selecting a first and a second molecular target from a pathway related to cancer; (ii) providing a first binding agent capable of binding a first molecular target; (iii) scoring a patient by assessing the amount of the first binding agent in a tissue, cells or bodily fluid in a patient; (iv) selecting a patient for administration of a therapeutic dose of a second binding agent capable of binding a second molecular target, wherein the patient is selected if the score is above a threshold and wherein the score above a threshold is indicative of cancer.

In one aspect, a method for identifying a patient for cancer therapy includes administering a diagnostic dose of a detectably labeled first binding agent to a patient. The detectably labeled first binding agent is capable of binding a cellular or molecular target (e.g., an extracellular portion of a cell surface target, e.g., PSMA). The method also includes selecting a patient for administration of a therapeutic dose of a second binding agent capable of binding a cellular target, where the selected patient exhibits a positive reading for the detectably labeled first binding agent.

In another aspect, a method for treating prostate cancer includes administering a diagnostic dose of a detectably labeled first binding agent to a patient. The detectably labeled first binding agent is capable of binding a molecular or cellular target (e.g., an extracellular portion of a cell surface target, e.g., PSMA). The method also includes administering a therapeutic dose of a second binding agent capable of binding a cellular target to a selected patient, where the selected patient exhibits a positive reading for the detectably labeled first binding agent.

In still another aspect, methods for treating cancer include providing instructions to administer to a patient a diagnostic dose of a detectably labeled first binding agent that is capable of binding a cellular target and/or providing instructions to assess the expression level of tumor marker or target molecule in a biological sample. In some embodiments, tumor cells are collected from blood sample or other bodily fluid samples and assessed for the presence and expression level of the target molecule. The methods also include providing instructions to administer a therapeutic dose of a second binding agent capable of binding a cellular target to a patient selected based on the level of first binding agent in the patient or in a biological sample obtained from the patient.

In some aspects, the invention includes methods for improving statistical significance of a clinical trial. In one aspect, the invention includes methods for reducing a number of patients required for a clinical trial. In some embodiments, the methods include administering a diagnostic dose of a detectably labeled first binding agent to a plurality of patients. The detectably labeled first binding agent is capable of binding a cellular target. The patient or patients are selected based on the level of first binding agent in the patient or in a biological sample obtained from the patient. Certain patients having been administered the diagnostic dose of a detectably labeled first binding agent are not selected and therefore are not administered the therapeutic dose of the second binding agent. The method also includes administering a therapeutic dose of a second binding agent capable of binding a cellular target to the selected patients. By selecting a patient or patients most likely to respond to the therapeutic dose of the second binding agent and de-selecting or excluding patients less likely or unlikely to respond favorably to the therapeutic second binding agent, one thereby improves the ability of the trial to reach statistical significance within a smaller number of treated patients.

In another aspect, the invention includes kits for selecting a patient for cancer therapy. In some embodiments, the kits include instructions for administering a diagnostic dose of a detectably labeled first binding agent that is capable of binding a cellular target or/and instructions for assessing the expression level of tumor marker or target molecule in a biological sample. The kits also include instructions for administering a therapeutic dose of a second binding agent to a selected patient. In other embodiments, the kits include instruction for assaying a biological sample with a detectably labeled first binding agent, the detectably labeled binding agent being capable of binding a molecular target and instruction for selecting a patient for administration of a therapeutic dose of a second binding agent capable of binding a second molecular target, wherein the selected patient exhibits a positive reading for the detectably labeled first binding agent. The patient or patients are selected based on the level of first binding agent in the patient or in a biological sample obtained from the patient.

In yet another aspect, the invention includes methods for selecting a patient for cancer therapy, wherein the patient is selected without administering a toxic therapeutic agent to the patient. In some embodiments, the methods include administering a detectably labeled binding agent to a patient. The detectably labeled binding agent is capable of binding a cellular target. The methods also include selecting a patient for treatment with a therapeutic conjugate comprising the binding agent and a cytotoxic or cytostatic therapeutic agent. The patient is selected based on the level of first binding agent in the patient or in a biological sample obtained from the patient.

In another aspect, the invention includes methods for selecting a treatment group of patients, wherein the patients are selected without administering a toxic therapeutic agent to the patients. In some embodiments, the methods include administering to a first group of patients a binding agent, wherein the binding agent is detectably labeled and is capable of binding a cellular target, and wherein the first group of patients has or is suspected of having a condition. The methods also include selecting patients for treatment of the condition with a therapeutic conjugate comprising the binding agent and a cytotoxic or cytostatic therapeutic agent. The patients are selected based on the level of first binding agent in a given patient or in a biological sample obtained from a given patient.

In still another aspect, the invention includes kits for cancer therapy. The kits include a diagnostic dose of a detectably labeled first binding agent to a patient, the detectably labeled binding agent being capable of binding a molecular target. The kits also include instruction for selecting a patient for administration of a therapeutic dose of a second binding agent capable of binding a molecular target, wherein the selected patient exhibits a positive reading for the detectably labeled first binding agent. In other embodiments, the kits include a detectably labeled first binding agent, the detectably labeled binding agent being capable of binding a molecular target and instructions for selecting a patient for administration of a therapeutic dose of a second binding agent capable of binding a second molecular target, wherein the selected patient exhibits a positive reading for the detectably labeled first binding agent.

In other embodiments, any of the aspects above, or any method or kit described herein, can include one or more of the following features.

The target can be an intracellular target or a cell surface target. In various embodiments, the condition or cancer is prostate cancer and the cell surface target is Prostate Specific Membrane Antigen (PSMA). In other embodiments, the cancer is non-prostate cancer and the cell surface target is a marker that is known to be present on the cells of the particular type of cancer. In one exemplary embodiment, the non-prostate cancer can include a solid tumor associated with PSMA expressing neo-vasculature and the cell surface target can be the PSMA on the neo-vascular cells.

In preferred embodiment, selecting a patient include detecting the molecular or cellular target using a first binding agent. Selecting a patient can include quantifying an amount of the molecular or cellular target in the patient or can include a qualitative assay of the cellular target in the patient. As described herein, the level of expression of the cellular or therapeutic target can be measured in vitro (e.g. diagnostic assay) or in vivo (e.g. in vivo imaging) using a detectably labeled first binding agent that is capable of binding the target. Diagnostic assays are frequently performed on biological samples removed from patients. Preferably, these samples are obtained in a minimally invasive manner, for example serum or urine samples. In vivo imaging technologies provide non-invasive methods for determining the state of a particular disease in the human body. Standard imaging techniques include but are not limited to magnetic resonance imaging, computed tomography scanning, PET, SPECT and the like.

In some embodiments, the level of expression of the cellular or therapeutic target is measured in vitro in a biological sample. Typically the level of the marker in a biological sample obtained from the patient is different (i.e., increased or decreased) from the level of the same marker in a similar sample obtained from a healthy individual. The sample can be derived from any biological source, such as tissues, extracts, or cell cultures, including cells (e.g. tumor cells), cell lysates, and physiological fluids, such as, for example, whole blood, plasma, serum, saliva, ocular lens fluid, cerebral spinal fluid, sweat, urine, milk, ascites fluid, synovial fluid, peritoneal fluid and the like. The sample can be treated prior to use, such as preparing plasma from blood, diluting viscous fluids, and the like. For example, cells or body fluid containing cells obtained from a subject can be contacted with a radiolabeled, or otherwise detectable and/or measurable, first binding agent in vitro. In other embodiments, a detectably labeled first binding agent is administered to a patient and the level of detectable label is observed in situ. The method can be an in vivo or ex vivo non-invasive method.

In various embodiments, any of the diagnostic (e.g., identifying or selecting) methods can also include administering a therapeutic dose of the second binding agent to the patient. The first and/or second binding agent can be an antibody or antigen binding portion or derivative thereof. The antibody or antigen binding portion or derivative thereof can be capable of binding the extracellular domain of PSMA.

In some embodiments, the detectable label includes an isotope selected from the group consisting of $^{177}$Lu, $^{111}$Indium, $^{67}$Cu, $^{18}$F, $^{99m}$Tc, $^{124}$I, $^{125}$I and $^{131}$I. The detectable label can be a Positron Emission Tomography (PET) agent including but not limited to $^{124}$I, $^{89}$Zr, etc. In certain embodiments, the first and/or second antibody or antigen binding portion or derivative thereof is radiolabeled. The radiolabel can be at least one of $^{177}$Lu, $^{111}$Indium, $^{67}$Cu, $^{18}$F, $^{99m}$Tc, $^{124}$I, $^{125}$I, $^{131}$I, and $^{99m}$Tc. In other embodiments, the first binding agent can be labeled with a dye or any other detectable agent known by those in the art.

In various embodiments, the antibody or antigen binding portion or derivative thereof is a monoclonal antibody or antigen binding portion or derivative thereof produced by a hybridoma selected from the group consisting of a hybridoma deposited under ATCC deposit accession number HB-12101, a hybridoma deposited under ATCC deposit accession number HB-12109, a hybridoma deposited under ATCC deposit accession number HB-12127, and a hybridoma deposited under ATCC deposit accession number HB-12126. The first and/or second binding agent has an affinity of at least about $10^{-9}$M for the target (e.g., cell surface target). The first binding agent and the second binding agent can be substantially the same.

In some embodiments, selecting a patient includes quantifying an amount of the target (e.g., cell surface target) in the patient's tumor sites. Quantifying can utilize a quantitative or semi-quantitative method. Selecting a patient can include in vivo imaging of the detectably labeled first binding agent. Selecting a patient can include a qualitative analysis of the target (e.g., cell surface target) in the patient. The method can include administering an image contrast agent in conjunction with the diagnostic dose of a detectably labeled first binding agent. It can also include other forms of anatomic imaging modalities (e.g., CT and/or MRI) that can be combined with imaging the first binding agent (e.g., PET-CT, SPECT-CT, planar image-MR, etc.).

In certain embodiments, the therapeutic dose of the second binding agent is administered to the selected patient without any restriction regarding the time interval between the first diagnostic binding agent and the second therapeutic agent. In a preferred embodiment, the interval should be less than or equal to 3 months, or less than or equal to 1 month or less than or equal to 2 weeks.

In various embodiments, a kit can include (e.g., in a diagnostic and/or therapeutic dose) a detectably labeled first binding agent, a second binding agent, and/or an image contrast agent. The first binding agent and the second binding agent can be substantially the same.

The various embodiments described herein can be complimentary and can be combined or used together in a manner understood by the skilled person in view of the teachings contained herein. Other aspects of the invention will become apparent from the following drawings and description, all of which illustrate principles of the invention, by way of example only.

BRIEF DESCRIPTION OF THE DRAWINGS

The patent and application filed contains at least one drawing executed in color. Copies of this patent or patent application publication with color drawings will be provided by the Office upon request and payment of the necessary fee.

FIG. 7 shows whole body images of scans taken after administration of $^{99m}$Tc-MDP (bone scan) and $^{177}$Lu-J591 mAb (left two and right two images, respectively).

FIG. 11 shows a graph of PSA response after treatment versus J591 imaging score (0-3+).

DETAILED DESCRIPTION OF THE INVENTION

Figure 1:
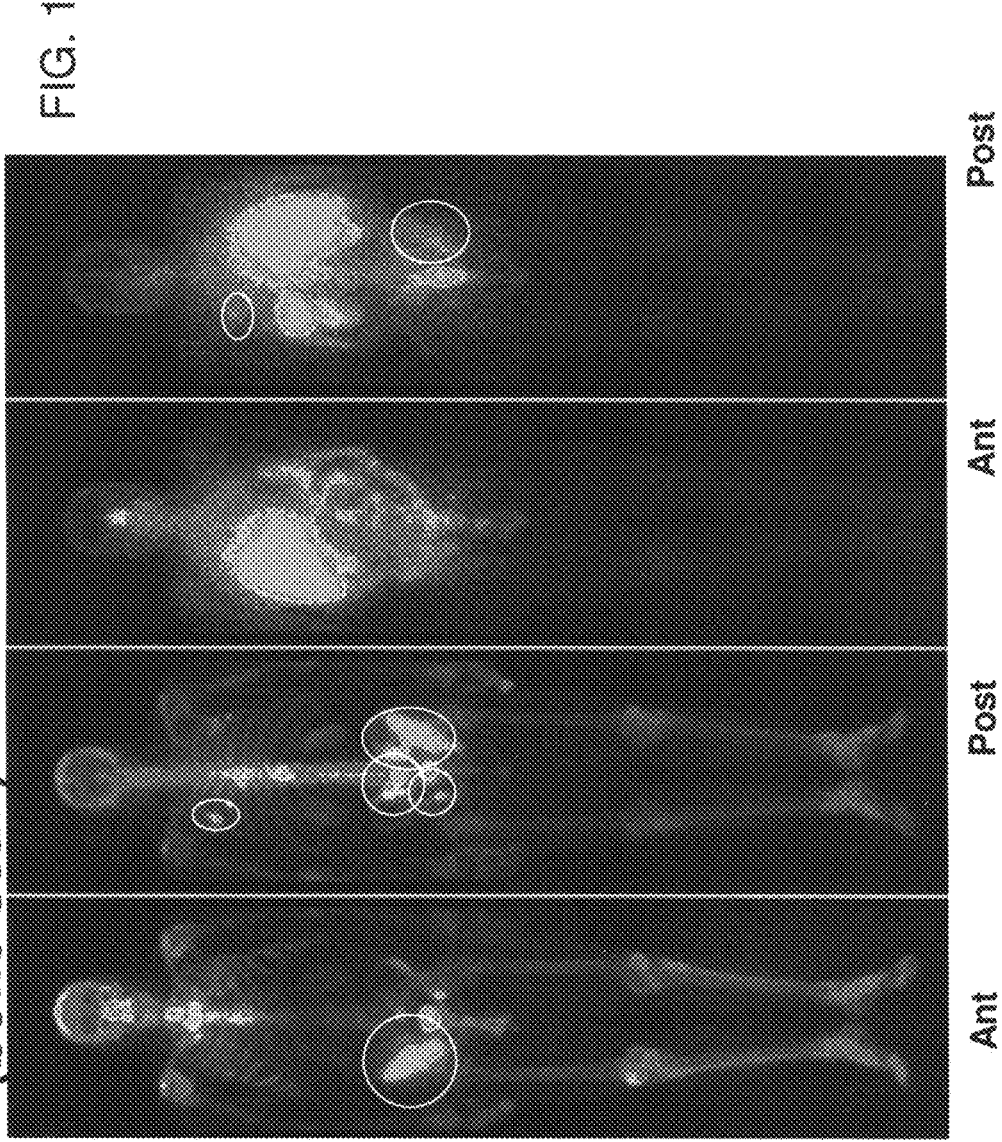
FIG. 1 shows whole body images of the same patient taken after administration of $^{99m}$Tc-MDP for a bone scan and $^{177}$Lu-J591 mAb (left two and right two images, respectively).

Provided herein are methods of identifying a suitable patient or patients for therapy such as cancer therapy. Aspects of the invention are directed to methods and kits for diagnosing the presence of cancer within a patient or subject, and for selecting the patient or subject who has cancer for therapy. Aspects of the invention can be used with a wide variety of cancers. Cancers include, but are not limited to, pancreatic cancer, melanomas, breast cancer, lung cancer, bronchus cancer, colorectal cancer, prostate cancer, pancreas cancer, stomach cancer, ovarian cancer, urinary bladder cancer, brain or central nervous system cancer, peripheral nervous system cancer, esophageal, cancer, cervical cancer, uterine or endometrial cancer, cancer of the oral cavity or pharynx, liver cancer, kidney cancer, testicular cancer, biliary tract cancer, small bowel or appendix cancer, salivary gland cancer, thyroid gland cancer, adrenal gland cancer, osteosarcoma, chondrosarcoma, cancer of hematological tissues, glioma, lymphoma and the like.

Some embodiments of the invention are directed to a method for diagnosing cancer by detecting the presence, expression level of a molecular target wherein the molecular target are from a particular pathway related to cancer. In some embodiments, the methods comprise scoring the presence, abundance or level of expression as being above a certain threshold with the score being indicative of cancer. The methods can be used to diagnose cancer and predict whether a patient or subject will benefit from cancer therapy. The methods can be used for diagnosis and treatment strategy for a patient suspected to have cancer. The molecular targets can come from any cancer associated pathway such as, for example, a pathway involved in the regulation of cancer. In some embodiments, the methods comprise assessing the expression level of a tumor marker or target in a patient using in vivo imaging and/or diagnostic assay or biological sample. A "marker" is a nucleic acid or protein which may be altered, wherein said alteration is associated with cancer. The alteration may be in amount, structure, and/or activity in a cancer tissue or cancer cell, as compared to its amount, structure, and/or activity, in a normal or healthy tissue or cell (e.g., a control), and is associated with a disease state, such as cancer. Marker molecules produced by cancers include monoclonal immunoglobulins, hormones, secreted serum proteins, antigens, enzymes and isoenzymes, cell surface markers, glycoproteins and carbohydrates, extracellular matrix proteins, mucins and nucleic acids (e.g. mRNA, DNA, microRNA). In some embodiments, the detection of the methylation state of a target gene(s) can be used. Cancer markers may be categorized as soluble markers, which appear in bodily fluids such as blood, plasma, serum, effusions, and urine. Other cancer markers are cell-associated proteins and nucleic acids that characteristically are not released into serum or other body fluids in any significant amounts. Cell- or tissue-associated tumor markers are detectable in tissue samples containing cancerous cells, or in biological samples that contain such cells. As used herein, the term "tumor marker" is used as an indicator of the presence of, or extent of, a cancerous growth or tumor. Example of tumor markers include but are not limited to PSA for prostate cancer, CA 125 for ovarian cancer, CA 195 for gastrointestinal cancers. Tumor markers may be cancer-specific markers (e.g. CA19-9, CA 125, CEA) or tissue-specific markers (e.g. PSA for prostate cancer, CA15-3 for breast cancer).

In some embodiment, the patient or biological sample obtained form the patient is assessed for the presence of the specific molecular target. As used herein, the term "assessing" includes any form of measurement, and includes determining if a molecule is present or not. The terms "determining," "measuring," "evaluating," "assessing," and "assaying" are used interchangeably and includes quantitative, qualitative and imaging determinations establishing the presence or absence of cancer associated target. Assessing may be relative or absolute. In some embodiments, the methods comprise scoring or quantifying the level of a first molecular target. In some embodiments, the methods comprise determining if the level is higher or lower as compared to a reference sample (e.g. healthy subject or biological sample obtained from a health subject) whether quantitatively, semi-quantitatively or qualitatively. In some embodiments, the methods comprise determining a quantitative tumor targeting index (TTI).

In some embodiments, the methods include administering a diagnostic dose of a detectably labeled first binding agent to a patient. The detectably labeled first binding agent is capable of binding, for example, to a cellular or molecular target. In some embodiments, the cellular target, also referred to herein as a therapeutic target, is an extracellular portion of a cell surface target. One or more patients are selected for administration of a therapeutic dose of a second binding agent capable of binding to a molecular or cellular target (e.g., the extracellular portion of the cell surface target). The patient or patients are selected based on the level of first binding agent in the patient or in a biological sample obtained from the patient. The invention also includes kits for use in identifying and/or treating patients according to the methods provided herein.

In various embodiments, methods can include: (i) identifying a first group of one or more patients developing, having, or suspected of having a cancer; (ii) administering a diagnostic dose of a detectably labeled first binding agent to each patient in the first group, where the detectably labeled first binding agent is capable of binding a molecular or cellular target for the cancer; (iii) observing the level of the detectably labeled first binding agent in each patient in the first group (e.g., quantitatively or semi-quantitatively measuring the target); (iv) selecting a second group of patients from the first group for a cancer therapy, based upon the level of detectably labeled first binding agent observed in the patient; and (v) administering a therapeutic dose of a second binding agent to one or more patients in the second group. In some of the methods provided herein, a diagnostic dose of a detectably labeled first binding agent is administered to one or more patients. A therapeutic dose of a second binding agent is then administered to selected patients that were administered the detectably labeled first binding agent.

In other embodiments, methods include (i) identifying a first group of one or more patients developing, having, or suspected of having a cancer; (ii) obtaining a biological sample for each patient of the first group (iii) assaying the biological sample for the presence of a first binding agent in each patient in the first group, where the first binding agent is capable of binding a molecular or cellular target for the cancer; (iv) assessing the level of the first binding agent in each biological sample (e.g., quantitatively or semi-quantitatively measuring the target); (v) selecting a second group of patients from the first group for a cancer therapy, based upon the level of first binding agent observed in the patient; and (vi) administering a therapeutic dose of a second binding agent to one or more patients in the second group. In some embodiments, the first binding agent comprises a label moiety (e.g. detectably labeled). The biological sample may be blood or other bodily fluids such as urine, cerebrospinal fluid, semen, etc. . . .

In a variety of embodiments, including kits and methods, the first binding agent and the second binding agent or therapeutic target binding portions thereof are, or may be, substantially the same. Alternatively, the second therapeutic binding agent may bind to a molecular or cellular target different from the first binding agent wherein the two different targets are functionally related. In some embodiment, the first binding agent may recognize a member or members of a genomic, proteomic, metabolomic or epigenomic signature associated with a specific disease. Signatures include, for example, the presence and/or levels and/or post-translation modification of a protein or collection of proteins; the presence and/or level of a nucleic acid; and the integrity or methylation status or other parameter of a nucleic acid. In an exemplary embodiment, the first binding agent may identify the level of a given metabolic or other gene or gene product in a functional pathway, signaling pathway or regulatory pathway.

The second therapeutic agent may target the same or a different molecule in the pathway. For example, the first binding agent may identify the level of the androgen receptor (AR) whereas the second therapeutic agent may act at any point of the androgen signaling pathway. In another embodiment, the first binding agent may recognize a member or members of a genomic, proteomic, metabolomic or epigenomic signature associated with a preferable method of treatment or targeted therapy. For example, the first binding agent can be used, in vivo imaging or diagnostic assay, to reflect the presence of a relevant genomic, proteomic, metabolomic or epigenomic signature and thereby direct the selection of therapeutic approach for the patient. In some embodiments, the pathway signature may direct to combination of therapies using multiple compounds that target multiple pathways. In some embodiments, the level of the first binding agent can be shown to be predictive of the response to the second therapeutic binding agent.

In some aspects of the invention, the detectably labeled first binding agent and the second binding agent are capable of binding a therapeutic target. The therapeutic target can be associated, directly or indirectly, with a condition such as a cancer. Suitable therapeutic targets include any extracellular or intracellular molecule or structure. In some embodiments, the therapeutic target is an antigen. The therapeutic target can be, for example, an extracellular portion of a cell surface molecule (e.g., PSMA). In other embodiments, the therapeutic targets are enzymes that participate in signal transduction (e.g. tyrosine kinases).

The first and/or second binding agent can include a member of a binding pair, such as receptor/ligand, antibody/antigen, enzyme/substrate, small molecule/ligand, and the like. The first and/or second binding agent can include a peptide or an aptamer designed and/or selected to bind the diagnostic and/or therapeutic target. Aptamers include nucleic acids (e.g. DNA or RNA) or peptide aptamers. In some embodiments, the first and/or second binding agent is a ligand for a cell surface receptor, or a substrate for a cell-associated molecule, or an antibody or antigen binding portion or derivative thereof that is capable of binding the therapeutic target. In an exemplary embodiment, the first and/or second binding agent is antibodies or derivatives thereof. In other embodiments, the first and/or second binding agent is small molecules or derivatives thereof. Small molecules have the advantage to pass through membranes and reach targets inside the cells. For example, the first and/or second biding agent can include a reversible (e.g. gefitinib or Iressa®) or an irreversible tyrosine kinase inhibitor. Tyrosine kinase inhibitors bind to the ATP-binding sites on the tyrosine kinase receptor preventing activation of the receptor and signal transduction from the receptor. Examples of small molecules include, but are not limited to Imatinib or Gleevec® which binds to the ATP binding site of bcr-abl, Gefitinib or Iressa® which is a selective inhibitor of epidermal growth factor receptor's (EGFR) tyrosine kinase domain, Erlotinib or Tarceva® which binds in a reversible fashion to the adenosine triphosphate (ATP) binding site of the epidermal growth factor receptor (EGFR) tyrosine kinase, bortezomib or Velcade® which is a tripeptide blocking binds the catalytic site of the 26S proteasome or any other small molecules (e.g. synthesized by rational design). In some embodiments, the first and/or second binding agent can be a hormone such as testosterone (e.g., dihydrotestosterone). For example, a detectably labeled first binding agent can be dihydrotestosterone conjugated to an imaging agent such as a PET imaging agent.

In some embodiments, the first and/or second binding agent can have an affinity for at least a portion of the therapeutic target, the affinity being stronger than about $10^{-7}$, $10^{-8}$, $10^{-9}$, or $10^{-10}$ M. The second binding agent can include a naked binding agent or a conjugated, derivatized, or labeled binding agent (e.g., a binding agent coupled to a therapeutic agent and/or label).

The therapeutic target may be located within the cell, as opposed to the exterior of the cell. In some embodiments, the first binding agent is selected such as it is able to traverse the cell membrane by passive diffusion or active transport across the cell membrane. In some embodiments, the first binding agent is a small molecule. In preferred embodiment, the first binding agent is labeled and the patient is subsequently imaged. Absent or low uptake indicates absent or weak presence of the target; moderate or high uptake of the labeled first binding agent indicates increased presence of the target. Selection of patients with increased presence of the target in preference to patients with weak presence or absence of the target would predict greater likelihood to respond to the second therapeutic binding agents.

The detectable label of labeled first binding agent can be essentially any agent capable of being qualitatively, semi-quantitatively, or quantitatively detected or measured. The detectable label can be any agent suitable for in vivo imaging. In some embodiments, the detectable label can be any agent suitable for in vitro and/or in vivo imaging. Imaging can include any one or more of: planar radionuclide imaging, positron emission tomography (PET), echo-planar imaging (EPI), single photon emission computed tomography (SPECT), sonographic imaging (e.g., radiation-free, contrast-specific, high frequency, two-dimensional), magnetic resonance imaging (MRI, also referred to as magnetic resonance tomography or MRT), X-ray, computed tomographic (CT) scans, fluorescence imaging, near-infrared imaging and other medically useful or adaptable imaging techniques.

The detectable label can be an agent suitable to the selected imaging method. For example, a radiolabel can be at least one of $^{177}$Lu, $^{99m}$Tc, $^{111}$In, $^{67}$Cu, $^{18}$F, $^{124}$I, $^{131}$I, and $^{89}$Zr, any of the radiolabels discussed below in connection with labeled reagents, or any other medically useful or adaptable radiolabel. In some embodiments, the detectable label has therapeutic effect when a sufficient dose is administered. However, it is not necessary for the detectable label or the first binding agent to have any independent therapeutic effect (e.g., kills or ablates cancer cells). In other embodiments, suitable detectable labels can include, for example, a fluorescent label, a near-infrared label, a biologically active enzyme label, a luminescent label, or a chromophore.

In some embodiments the detectable label of the labeled first binding agent and the therapeutic agent of the conjugated second binding agent are the same. In some embodiments, the detectable label of the labeled first binding agent and the therapeutic agent of the conjugated second binding agent are $^{177}$Lu. $^{177}$Lu is radionuclide having a low β-energy emission (e.g., about 0.497 MeV) with relatively short therapeutic range and a γ emission (e.g., about 0.113 and 0.208 MeV) that allows imaging. In some cases, $^{177}$Lu can be used (even at relatively high doses) without substantial bone marrow toxicity. In some cases, $^{177}$Lu is suitable for treating small tumors (e.g., about 2-3 mm).

In various embodiments, the condition or cancer is prostate cancer and the cell surface target is Prostate Specific Membrane Antigen (PSMA). In other embodiments, the cancer is non-prostate cancer and the cell surface target is a marker that is known to be present on the cells of the particular type of cancer. In one exemplary embodiment, the non-prostate cancer can include a solid tumor associated with PSMA expressing neo-vasculature and the cell surface target can be the PSMA on the neo-vasculature cells.

In one embodiment, after administering the diagnostic dose of the detectably labeled first binding agent to the patient, the level of detectably labeled first binding agent present in the patient is observed using a suitable assay or detection method for the detectable label. The level of detectable label can be observed, for example, by subjecting the patient to a suitable imaging method. In another embodiment, after assaying a biological sample obtained from the patient using a detectably labeled first binding agent, the level of detectably labeled first binding agent present in the sample is assessed using a suitable assay or detection method.

The level of expression or amount of the cellular target can be observed by detecting the level of detectably labeled first binding agent in the patient or in a biological sample obtained from the patient. As demonstrated herein, the level of first binding agent that binds or targets the therapeutic target in vivo is shown to be correlated to and predictive of the effect of treatment using a second binding agent. This allows the selection of a patient or patient population most likely to respond to treatment directed towards the therapeutic target. The correlation between level of first binding agent detected (diagnostic effect) and treatment effect was unexpected for many reasons. First, it had been reported that 100% of prostate cancers were PSMA-positive [Bostwick, D. G., et al., Cancer 82:2256-2261, 1998], that 98-100% of all metastatic PCa's were imaged by mAb to PSMA [Bander et al, J. Clin. Oncol. 2005, 23:4591-4601; Bander, N. H., et al., J. Urol. 2003, 170: 1717-1721], and that as a general rule all metastatic Pca's expressed higher levels of PSMA than localized lesions [Wright, G. L. et al., Urol. Oncol. 1995, 1: 18-28; Wright, G. L., et al., Urology 48:326-334, 1996; Sweat, S. D. et al., Urol., 52:637-640, 1998]. See also Horoszewicz, J S, et al., Anticancer Res. 1987. 7:927-936; Silver D. A. et al., Clin Can Res 1997. 3: 81-85; Chang S. S. et al., Urology, 2001. 57: 1179-83; Bostwick, D G, et al., Cancer 1998. 82: 2256-2261; Ross, J S, et al., Clin Can Res 2003. 9:6357-6362; Mannweiler, S, et al., Pathol. Oncol. Res. 2009. 15:167-172; and Ananias, Hildo J. K. et al., The Prostate 2009 10:1101-1108. This is very consistent with the imaging data in 137 patients in clinical trials who received mAb J591 specific for PSMA, none of whom were screened for PSMA expression as an entry criterion (Bander N. H. et al., J. Urol., 2003. 170:1717-1721; Milowsky M. I. et al., J. Clin. One., 2004; 22:2522-2531; Bander N. H. et al., J. Clin. One., 2005; 23:4591-4601; Scott T. et al., ASCO Proceedings, 2008. In those patients, the success rate of imaging was 95%. In virtually every patient, all lesions seen on conventional bone, CT and/or MRI were seen on J591 scan. This body of in vitro and in vivo data from multiple groups indicated that there were not identifiable subsets of patients based on PSMA expression. Furthermore, given the extremely heterogeneous biology of prostate cancer (ranging from patients who have sub-clinical disease detected only on autopsy to the other extreme where patients die rapidly as a result of their metastatic disease) and the intrinsic variability of cancers in general and prostate cancer specifically to respond to a given therapy, there was no expectation that a diagnostic study for PSMA expression (either in vitro or in vivo by imaging) would allow pre-treatment selection of patients more (or less) likely to respond to PSMA-targeted therapies. In addition, it was thought that response to a targeted therapeutic agent (radiolabeled or other cytotoxins) would be a function of many factors, including but not limited to the ability of the binding agent to reach the therapeutic target, ability of the therapeutic binding agent to penetrate into the tumor, clearance of the binding agent from the tumor cells, clearance of the binding agent from the body as well as the relative intrinsic sensitivity or resistance of the cancer to the respective radiolabel or other cytotoxins. Furthermore, relative sensitivity of the tumor to the radiolabel or other cytotoxins would not be expected to be predicted by detecting the level of targeting agent in the tumor or body. In addition, the results of cancer therapies have not previously been shown to be predictable on the basis of assessment of pre-treatment imaging studies or assay of binding in a biological sample.

In the case of non-prostate cancers, PSMA-expressing neo-vasculature was reported to be present in 95% of cases [Liu H. et al., Cancer Res. 1997, 57(17):3629-34; Chang, S. S. et al., Cancer Res., 59:3192-3198, 1999; Chang S. S. et al., Clin. Cancer Res. 1999, 5(10):2674-81] and Morris, M. et al. [Clin. Can. Res. 2007; 13:2707-2713] found that a radiolabeled antibody to PSMA was able to target in vivo 95% of unselected patients with metastatic solid tumors. More recently, we have found that approximately 65% of metastatic gastric cancers and 85% of metastatic colorectal cancers contain PSMA-expressing neo-vasculature [Haffner, M et al., Hum. Pathol., 40:1754-1761, 2009] and similar results were found in breast, ovarian and endometrial cancers—that is, a varying subset of patients with non-PCa tumors have PSMA-positive neo-vasculature. As a result, a subpopulation of patients having PSMA-positive non-Pca tumors (as evidenced by a non-invasive imaging study or biological sample assay) can be selected to be treated using a PSMA-targeted therapy and are more likely to respond favorably than patients whose tumors are PSMA-negative.

Observing the level of a therapeutic target in vivo using a detectably labeled first binding agent can be used to select patients who are predicted to benefit from therapy and to exclude patients who are not predicted to benefit from therapy. Patients who are not predicted to benefit from therapy can nevertheless benefit from the invention because they can be spared the potential side effects of the therapy not likely to be beneficial and they can be directed earlier to alternative treatments from which they may benefit. Patients who are predicted to benefit from the therapy can receive the therapy. Additionally, the patients who are predicted to benefit from the therapy can be included in a clinical trial. Particularly, imaging or reading the detectably labeled first binding agent can segregate patients by identifying, for example, varying levels of target antigen expression (e.g., by scoring the level or amount of target). A predetermined threshold of target can be set based upon a hypothesized or empirical relationship between the level of target and expected responsiveness to therapy (e.g., expression of PSMA above a threshold indicates a patient to be selected for therapy). Likewise, patients can benefit from the invention because in various embodiments it includes in vivo diagnostic methods that do not require a tissue biopsy (e.g., as opposed to in vitro assays such as immunohistochemistry, FISH, PCR, and the like, which can be used to select patients for targeted treatments such as trastuzumab and/or anti-EGFr). Another benefit is that the invention provides information on all of a patient's lesions rather than only a single lesion that is subjected to invasive, and potentially risky, biopsy. The invention further benefits patients who do not have a lesion accessible to biopsy. Another benefit is the ability to select a patient for earlier chemotherapy and/or more aggressive chemotherapeutic agent or regimen. Yet, another benefit is the ability to provide known prostate cancer PSMA-targeting therapy to patients having non-prostate cancer associated with the expression of PSMA (e.g., in the neo-vasculature of solid tumors).

In various embodiments, the selection of patients suitable for a therapy can be distinguished from selection of an appropriate dosage for a therapy (e.g., radio-immunotherapy using antibody therapeutics such as Iodine 131-Tositumomab, also known as BEXXAR®, is limited to determining an appropriate dose, and does not determine whether or not to treat a patient or predict how a patient will respond to a treatment).

In various embodiments, any of the diagnostic (e.g., identifying or selecting) methods can also include administering a therapeutic dose of the second binding agent to the patient. The first and/or second binding agent can be an antibody or antigen binding portion or derivative thereof. The antibody or antigen binding portion or derivative thereof can be capable of binding the extracellular domain of PSMA.

It should be apparent that the same procedures can be applied when the target is present on the neo-vascular endothelial cells and/or connective tissue cells adjacent to the tumor cells. One can similarly use the labeled first binding agent to determine the presence and relative or absolute amount of the target molecule in an individual patient's tumor and use that as a criterion to select patients with higher target levels to undergo treatment with the therapeutic second binding agent as these would be the subset of patients more likely to respond to the therapeutic second binding agent.

In some embodiments, the detectable label includes an isotope selected from the group consisting of $^{177}$Lu, $^{111}$Indium, $^{67}$Cu, $^{18}$F, $^{99m}$Tc, $^{124}$I, $^{125}$I, and $^{131}$I. The detectable label can be a Positron Emission Tomography (PET) agent including but not limited to $^{124}$I, $^{89}$Zr, etc.

In certain embodiments, the first and/or second antibody or antigen binding portion or derivative thereof is radiolabeled. The radiolabel can be at least one of $^{177}$I, $^{111}$Indium, $^{67}$Cu, $^{18}$F, $^{99m}$Tc, $^{124}$I, $^{125}$I, $^{131}$I, and $^{99m}$Tc. In other embodiments, the first binding agent can be labeled with a dye or any other detectable agent known by those in the art.

In various embodiments, the antibody or antigen binding portion or derivative thereof is a monoclonal antibody or antigen binding portion or derivative thereof produced by a hybridoma selected from the group consisting of a hybridoma deposited under ATCC deposit accession number HB-12101, a hybridoma deposited under ATCC deposit accession number HB-12109, a hybridoma deposited under ATCC deposit accession number HB-12127, and a hybridoma deposited under ATCC deposit accession number HB-12126. The first and/or second binding agent has an affinity of at least about $10^{-9}$ M for the target (e.g., cell surface target). The first binding agent and the second binding agent can be substantially the same.

In some embodiments, selecting a patient includes quantifying an amount of the target (e.g., cell surface target) in the patient's tumor sites. Quantifying can utilize a quantitative or semi-quantitative method. Selecting a patient can include in vivo imaging of the detectably labeled first binding agent. Selecting a patient can include a qualitative analysis of the target (e.g., cell surface target) in the patient. The method can include administering an image contrast agent in conjunction with the diagnostic dose of a detectably labeled first binding agent. It can also include other forms of anatomic imaging modalities (e.g., CT and/or MRI) that can be combined with imaging the first binding agent (e.g., PET-CT, SPECT-CT, planar image-MR, etc.).

In various embodiments, a period of time between administering the diagnostic dose of the detectably labeled first binding agent and observing the level of the detectably labeled first binding agent in the patient may be necessary. The time between administering the detectably labeled first binding agent and observing the level of the detectably labeled first binding agent in the patient can be determined by one of ordinary skill in the art based on the nature of the first binding agent and/or the detectable label. For example, a suitable amount of time for observing the level can be determined by factors including the localization of the detectably labeled first binding agent, the amount of background noise associated with a signal of the detectably labeled first binding agent, the affinity of the detectably labeled first binding agent for the therapeutic target, the metabolism of the detectably labeled first binding agent, and the size of the detectably labeled first binding agent. The suitable amount of time can be on the scale of hours to weeks (e.g., about 1 or 2 hours, several days or weeks).

In some embodiments, the level of detectable label in the patient is observed and a qualitative score is assigned to the patient based on the relative amount of label deemed to be present. For example, where an imaging method is used to observe the detectable label in the patient, the image obtained can be scored as 0, 1+, 2+, or 3+ where 3+ is assigned to the highest levels of label detected and 0 is assigned to images of patients who did not show visible targeting of the lesion/s. In some embodiments, the images are scored visually (e.g., by a medical professional such as a radiologist or oncologist). In one embodiment (e.g., $^{111}$In-J591 or $^{177}$Lu-J591), patient images are visually scored by a physician as follows: 0=an image/sample of patient who do not show any visible targeting of a lesion (e.g., tumor undetectable), 1+=an image/sample with a faint or weak tumor uptake wherein the detectable tumor uptake is equal to or less than that of the control wherein tumor uptake is clearly present, 2+=an image/sample having moderate uptake wherein the detectable tumor uptake is less than that of liver, 3+=an image/sample having a strong tumor uptake wherein the detectable tumor uptake is equal to or greater than the amount in liver.

Based upon the level of detectable label in the patient, a patient is selected for administration of a therapeutic dose of a second binding agent capable of binding an extracellular or intracellular target. In some embodiments, the second binding agent capable of an extracellular portion of the cell surface target. In particular, where the selected patient exhibits a positive reading for the detectably labeled first binding agent, the patient is selected for administration of a therapeutic dose of a second binding agent. In various embodiments the positive reading can be a predefined response (e.g., a score above a certain threshold). The positive response can be empirical (e.g., a score above which a patient has a reasonable probability of responding to treatment). In certain embodiments, a positive reading for the detectably labeled first binding agent can include a quantitative assay (e.g., a predetermined level or amount of the target). In some embodiments, a positive reading for the detectably labeled first binding agent can include a qualitative assay (e.g., a presence or absence of the target). The threshold can be determined by one of ordinary skill in the art, for example, by comparing readings in a series of patients obtained from the first binding agent and comparing those readings to response resulting from therapy with the second binding therapeutic agent. In such a manner, one can set and/or adjust the threshold to the point below which the likelihood of response minimizes the value of administering the second binding therapeutic agent. After selecting a patient based the level of detectable label observed, a therapeutic dose of a second binding agent can be administered.

In various embodiments, a period of time between administration of the therapeutic dose and subsequent patient selection is allowed to pass. The time between selecting the patient and administering the therapeutic dose of a second binding agent can be determined by one of ordinary skill in the art based, for example, on the condition of the patient, the nature of the first binding agent, and/or nature of the second binding agent, including any therapeutic agent associated with the second binding agent. In one embodiment, the therapeutic dose can be administered immediately after observing the level of the detectable label in the patient. This choice can include rapid treatment of the cancer and potential for reduced cost (e.g., fewer trips to the hospital or clinic, and less time consumed by the physician and patient). In some embodiments, it is possible for the diagnostic dose and the therapeutic dose to be administered during a single visit to the hospital or clinic. In another embodiment, the administration of the therapeutic dose can be separated from the time of observing the level of detectable label in the patient by days, weeks, or months. In certain situations, such a separation can be desirable (e.g., wait for a patient to be a stronger candidate for therapy, for example, by overcoming anemia or another physical condition).

The therapeutic dose of the second binding agent can be administered to a patient (also referred to herein as a subject) in single or multiple doses to treat or prevent progression of a prostatic or cancerous disorder. The dose or doses can be chosen in accordance with different parameters, in particular in accordance with the mode of administration used and the state of the subject. Other factors include the desired period of treatment, and whether other forms of treatment are being co-administered or used in conjunction with the therapeutic dose.

In some embodiments, the therapeutic dose of the second binding agent is administered in amount sufficient to inhibit the growth of the cancer cells or to kill the cancer cells. In general, where the second binding agent is an antibody or antigen-binding portion thereof, a therapeutic dose can range from about 1 to about 1000 mg. In some embodiments, an antibody is administered to the patient in sufficient amount to achieve a serum concentration of at least about 0.005-5 µg/mL of antibody in the subject. In some embodiments, the antibody or antigen binding portion or derivative thereof is administered in sufficient amount to achieve a serum concentration of 10, 25, 50, 100, or 200 µg/mL. In some embodiments, an antibody or antigen binding portion or derivative thereof is an antigen binding portion of an antibody, such as a $(Fab')_2$ and is administered to the patient in sufficient amount to achieve a serum concentration of at least about 0.003 to at least about 3.3 µg/mL of the antigen binding portion or derivative thereof in the subject. In some embodiments the $(Fab')_2$ is administered to achieve a serum concentration of 6.6, 10, 20, 40, or 80 µg/mL. In some embodiments, the antibody or antigen binding portion thereof is administered in sufficient amount and frequency to achieve a sustained serum concentration of the desired amount.

The second binding agent can be administered to the subject such that the serum level of the second binding agent is sustained for the desired period of time. The desired serum level can be based on the amount of second binding agent that can be measured in a sample of blood, serum or plasma or can be based, for example on a desired outcome, such as inhibition of the growth of the cancer cells (e.g. cytostatic effect) or killing of the cancer cells (e.g. cytotoxic effect). The dose of second binding agent can be adjusted by one or ordinary skill in the art based, for example on the size of the binding agent, and the binding affinity of the binding agent and the target. A suitable level of binding agent in the serum can be maintained by way of repetitive dosing.

In some embodiments, serum trough and/or peak levels of binding agent can be determined prior to administering the next dose of binding agent. Serum trough and/or peak levels can be determined using standard techniques known in the art. Serum trough and/or peak levels can be used to adjust the prescribed dose of binding agent to individual patients or groups of patients.

A variety of routes can be used to administer the first or second binding agent. The particular mode selected will depend upon the particular drug selected, the severity of the disease state being treated and the diagnostic or therapeutic dosage required. The methods of this invention, generally speaking, may be practiced using any mode of administration that is medically acceptable, meaning any mode that produces effective levels of the active compounds without causing clinically unacceptable adverse effects. Such modes of administration include oral, rectal, sublingual, topical, nasal, transdermal or parenteral routes. The term "parenteral" includes subcutaneous, intravenous, intramuscular, intraperitoneal, or infusion.

The therapeutic dose of the second binding agent can be administered once, continuously, such as by continuous pump, or at periodic intervals. The periodic interval may be weekly, bi-weekly, tri-weekly or monthly. The dosing can occur over the period of one month, two months, three months or more to elicit an appropriate therapeutic response. Desired time intervals of multiple doses of a particular composition can be determined without undue experimentation by one skilled in the art.

In some embodiments, the first and/or second binding agent can be conjugated or linked (e.g., by a cleavable linker or a non-cleavable linker) to another molecular entity, typically a detectable label or a therapeutic (e.g., a cytotoxic or cytostatic) agent. The first and/or second binding agent can be functionally linked (e.g., by chemical coupling, genetic fusion, non-covalent association or otherwise) to one or more other molecular entities (e.g., diagnostic or therapeutic). The use of a cleavable linker allows the release of the therapeutic agent into the intracellular cytoplasm upon internalization of the conjugated second binding agent. A non-cleavable linker would allow release upon digestion of the conjugated second binding agent or can be used with an agent that does not require release from the second binding agent.

In some embodiments, the second binding agent comprises a toxic therapeutic agent. The therapeutic agent can be any compound suitable to treat the condition, for example by inhibiting growth of the cancer cells, or killing the cancer cells. Suitable therapeutic agents include, for example, a cytotoxic moiety such as a therapeutic drug, a radioisotope, molecules of plant, fungal, or bacterial origin, or biological proteins (e.g., protein toxins) or particles (e.g., nano-particles or recombinant viral particles such as a viral coat protein), or mixtures thereof. The therapeutic agent can be an intracellularly active drug or other agent, such as short-range radiation emitters, including, for example, short-range, high-energy α-emitters, as described herein. Suitable radioisotope include an α-, β-, or γ-emitter, or β- and γ-emitter. Radioisotopes useful as therapeutic agents include yttrium ($^{90}$Y), lutetium ($^{177}$Lu), actinium ($^{225}$Ac), astatine ($^{211}$At), rhenium ($^{186}$Re), bismuth ($^{212}$Bi or $^{213}$Bi), and rhodium ($^{188}$Rh). Radioisotopes useful as labels (e.g., for use in diagnostics) include iodine ($^{131}$I, $^{124}$I or $^{125}$I), indium ($^{111}$In), technetium ($^{99m}$Tc), phosphorus ($^{32}$P), carbon ($^{14}$C), tritium ($^{3}$H), and zirconium ($^{89}$Zr) or one of the therapeutic isotopes listed above. In some embodiments, the second binding agent can be coupled to a molecule of plant or bacterial or fungal origin (or derivative thereof) such as a maytansinoid (e.g., maytansinol or the DM1 maytansinoid), a taxane, a calicheamicin or a duocarmicin. Where the second binding agent is an antibody or antigen binding portion thereof, the second binding agent can be linked to another antibody or antigen binding portion thereof to form e.g., a bispecific or a multispecific antibody.

In some embodiments, the second binding agent is coupled (e.g., by covalent linkage) to a proteosome inhibitor or a topoisomerase inhibitor. [(1R)-3-methyl-1-[[(2S)-1-oxo-3-phenyl-2-[(3-mercaptoacetyl) amino]propyl]amino] butyl] Boronic acid is a suitable proteosome inhibitor. N,N'-bis[2-(9-methylphenazine-1-carboxamido)ethyl]-1,2-ethanediamine is a suitable topoisomerase inhibitor. In some embodiments, the second binding agent can be used in combination with other therapies.

In some embodiments, other therapies include administering to the subject a cytotoxic or chemotherapeutic agent. Exemplary cytotoxic agents include antimicrotubule agents, topoisomerase inhibitors, antimetabolites, mitotic inhibitors, alkylating agents, intercalating agents, agents capable of interfering with a signal transduction pathway, agents that promote apoptosis, agents that interfere with folate metabolism and radiation. In some embodiments, the cytotoxic agent can be taxol, taxotere, cytochalasin B, gramicidin D, ethidium bromide, emetine, mitomycin, etoposide, tenoposide, vincristine, vinblastine, colchicin, doxorubicin, daunorubicin, dihydroxy anthracin dione, methotrexate, mitoxantrone, mithramycin, actinomycin D, 1-dihydrotestosterone, glucocorticoids, procaine, tetracaine, lidocaine, propranolol, puromycin, a maytansinoid such as maytansinol (see U.S. Pat. No. 5,208,020), CC-1065 (see U.S. Pat. Nos. 5,475,092, 5,585,499, 5,846,545) and/or analogs or homologs thereof.

Where the methods and compositions provided herein are used to treat patients having prostatic disorders such as prostate cancer, the second binding agent can be an antibody or antigen binding portion or derivative thereof that is capable of binding to an extracellular domain of PSMA and can be used in combination with existing therapeutic modalities such as prostatectomy (focal, partial or radical), radiation therapy, prostatic ablation therapy (e.g. hormonal therapy, cryosurgery, laser ablation, high intensity focused ultrasound, and the like), and cytotoxic chemotherapy as described above. Typically, hormonal therapy works to reduce the levels of androgens in a patient, and can involve administering a luteinizing hormone-releasing hormone (LHRH) analog or agonist (e.g., Lupron®, Zoladex®, leuprolide, buserelin, or goserelin), as well as antagonists (e.g., Abarelix). Non-steroidal anti-androgens including flutamide, bicalutimade, or nilutamide, can also be used in hormonal therapy, as well as steroidal anti-androgens (e.g., cyproterone acetate or megastrol acetate), estrogens (e.g., diethylstilbestrol), surgical castration, secondary or tertiary hormonal manipulations (e.g., involving corticosteroids (e.g., hydrocortisone, prednisone, or dexamethasone), ketoconazole, abiraterone, MDV3100 and/or aminogluthethimide), inhibitors of 5a-reductase (e.g., finasteride, dutasteride), herbal preparations, hypophysectomy, and adrenalectomy. Furthermore, hormonal therapy can be performed continuously, intermittently or using combinations of any of the above treatments (e.g., combined use of leuprolide and bicalutamide).

The methods of treating cancer provided herein can be used to treat any cancer, such as prostate cancer or solid tumors that comprises at least some cells that express PSMA on their cell surfaces. In humans, PSMA is expressed on the surface of normal, benign hyperplastic prostatic epithelial cells (e.g., benign prostate secretory-acinar epithelium), cancerous prostate epithelial cells (e.g., prostatic intraepithelial neoplasia and prostatic adenocarcinoma), and vascular endothelial cells proximate of certain cancerous cells. Such cancer types containing PSMA-positive vasculature include (but are not limited to), for example, renal, urothelial (e.g., bladder), testicular, colon, rectal, lung (e.g., non-small cell lung carcinoma), breast, liver, neural (e.g., neuroendocrine), glial (e.g., glioblastoma), pancreatic (e.g., pancreatic duct), ovarian, endometrial, melanoma (e.g., malignant melanoma), or soft tissue sarcoma cancerous cells. Examples of prostatic disorders that can be treated or prevented include, but are not limited to, genitourinary inflammation (e.g., prostatitis), benign enlargement, for example, nodular hyperplasia (benign prostatic hypertrophy or hyperplasia); and cancer (e.g., adenocarcinoma or carcinoma) of the prostate and/or testicular tumors, including recurrent prostate cancer. "Recurrence" or "recurrent" prostate cancer, refers to an increase in PSA levels after an anti-cancer treatment (e.g., prostatectomy and/or radiation) to greater than 0.4 ng/dL (or PSA levels less than 0.4 ng/dL, if more sensitive assays are used) in two consecutive tests spaced by a one month period. Cancer recurrence can occur within a short period of time from the anti-cancer treatment (e.g., immediately, a few weeks or months after treatment, or can occur several years after an anti-cancer treatment). For example, in prostate cancer patients, recurrence can happen several years after an anti-cancer treatment (e.g., up to about 4, 5, 6, 7, 8, 9, 10, 12, 14, 15 or more years after treatment). Recurrence can be classified as "local recurrence", "regional recurrence" or "distant recurrence." "Local recurrence" refers to cancers that recur in tissue or organs adjacent to or proximate to the primary cancerous tissue or organ. For example, in subjects having prostate cancer, local recurrence can occur in tissue next to the prostate, the prostatic fossa, in the seminal vesicles, the muscles next to the prostate, and/or the rectal wall. Regional recurrence could involve the surrounding lymph nodes in the pelvis and/or walls of the pelvis. "Distant recurrence" refers to cancers that recur distant from the cancerous tissue or organ. For example, in subjects having prostate cancer, distant recurrence includes cancers that spread to the bones or other organs at a distance from the primary site. The term "cancer" includes all types of cancerous growths or oncogenic processes, metastatic tissues or malignantly transformed cells, tissues, or organs, irrespective of histopathologic type or stage of invasiveness. In some embodiments, the cancerous cells or cells proximate to the cancerous cells (such as the vascular endothelial cells) express PSMA on their cell surface.

The methods of treating cancer provided herein can be used to treat non-prostatic cancer. Examples of non-prostatic cancerous disorders include, but are not limited to, solid tumors, soft tissue tumors, and metastatic lesions. Examples of solid tumors include malignancies such as sarcomas, adenocarcinomas, and carcinomas, of the various organ systems, such as those affecting lung, breast, lymphoid, gastrointestinal (e.g., colon), and genitourinary tract (e.g., renal, urothelial cells), pharynx, etc. Adenocarcinomas include malignancies such as most colon cancers, rectal cancer, renal-cell carcinoma, liver cancer, non-small cell carcinoma of the lung, cancer of the small intestine and cancer of the esophagus. Metastatic lesions of the aforementioned cancers can also be treated or prevented using the methods and compositions provided herein.

The term "antibody" includes a protein comprising at least one, and preferably two, immunoglobulin heavy (H) chain variable regions (abbreviated herein as VH), and at least one and preferably two immunoglobulin light (L) chain variable regions (abbreviated herein as VL) that is capable of specifically binding to a given antigen. As used herein, a "derivative" means that one or more atoms or portions of the molecule are changed from the referenced structure. As used herein, "specific binding" refers to the property of the antibody to bind to an antigen (e.g., PSMA) with an affinity of at least $10^7$ $M^{-1}$. In some embodiments, specific binding refers to the ability to bind to a specific antigen (e.g., human PSMA protein) with an affinity that is at least two-fold, 10-fold, 50-fold, 100-fold, 1000-fold, or more than its affinity for binding to an unrelated antigen other than or unrelated to the specific antigen. Accordingly, in some embodiments, specific binding to PSMA refers to the ability to bind to a specific PSMA (e.g., human PSMA protein) with an affinity that is at least two-fold, 10-fold, 50-fold, 100-fold, 1000-fold, or more than its affinity for binding to an unrelated antigen other than or unrelated to PSMA (e.g., BSA, casein, etc).

The VH and VL regions can be further subdivided into regions of hypervariability, termed "complementarity determining regions" ("CDR"), interspersed with regions that are more conserved, termed "framework regions" (FR). The extent of the framework region and CDRs has been precisely defined (see, Kabat, E. A., et al. (1991) Sequences of proteins of Immunological Interest, Fifth Edition, U.S. Department of Health and Human Services, NIH Publication No. 91-3242, and Chothia, C. et al. (1987) J. Mol. Biol. 196:901-917). In some embodiments, each VH and VL is composed of three CDRs and four FRs, arranged from amino-terminus to carboxy-terminus in the following order: FR1, CDR1, FR2, CDR2, FR3, CDR3, FR4.

The VH or VL chain of the antibody can further include all or part of immunoglobulin heavy or light chain constant regions. In one embodiment, the antibody is a tetramer of two immunoglobulin heavy chains and two immunoglobulin light chains. In some embodiments, the heavy and light chains are inter-connected by disulfide bonds. In some embodiments, the heavy chain constant region is comprised of three domains, CH1, CH2 and CH3. In some embodiments, the light chain constant region is comprised of one domain, CL. The variable region of the heavy and light chains contains a binding domain that interacts with an antigen such as the extracellular portion of PSMA or portion thereof. In some embodiments, the constant regions of the antibodies mediate the binding of the antibody to host tissues or factors, including various cells of the immune system (e.g., effector cells) and the first component (Clq) of the classical complement system. In this manner, the antibody can elicit an antibody-dependent cellular cytotoxic response and/or complement mediated cytotoxicity. The term "antibody" includes intact immunoglobulins of types IgA, IgG, IgE, IgD, IgM (as well as subtypes thereof), wherein the light chains of the immunoglobulin may be of types kappa or lambda.

The term "antigen binding portion or derivative thereof" includes any portion of an antibody molecule that specifically binds to the antigen (such as PSMA or an extracellular portion of PSMA). For example, an antigen binding portion of an antibody includes molecules in which one or more immunoglobulin chains is not full length but which is capable of specifically binding to the antigen. Examples of binding portions encompassed within the term "antigen binding portion or derivative thereof" include, for example, (i) a Fab fragment such as a monovalent fragment consisting of the VL, VH, CL and CH1 domains; (ii) a F(ab')$_2$ fragment, a bivalent fragment comprising two Fab fragments linked by a disulfide bridge at the hinge region; (iii) a Fd fragment consisting of the VH and CH1 domains; (iv) a Fv fragment consisting of the VL and VH domains of a single arm of an antibody, (v) a dAb fragment (Ward et al., (1989) Nature 341:544-546), which consists of a VH domain; and (vi) an isolated complementarity determining region (CDR) having sufficient framework capable of specifically binding to the antigen or an antigen binding portion of a variable region. An antigen binding portion of a light chain variable region and an antigen binding portion of a heavy chain variable region such as the two domains of the Fv fragment, VL and VH, can be joined, using recombinant methods, by a synthetic linker that enables them to be made as a single protein chain in which the VL and VH regions pair to form monovalent molecules (known as single chain Fv (scFv); see e.g., Bird et al. (1988) Science 242:423-426; and Huston et al. (1988) Proc. Natl. Acad. Sci. USA 85:5879-5883). Such single chain antibodies are also intended to be encompassed within the term "antigen binding portion thereof." Also encompassed in the term "antigen binding portion or derivative thereof" includes structural variants made from or derived from antibody such as diabodies, minibodies, single chain antibodies, etc. As used herein the term "minibody" refers to a recombinant antibody in which the heavy- and light-chain variable regions are part of the same polypeptide chain, which also includes the heavy-chain hinge region and one heavy-chain constant domain. The single chain may be dimerized, for example by disulfide linkages. As used herein the term "diabody" refers to a recombinant antibody that comprises the heavy- and light-chain variable regions joined by a flexible peptide linker, the linker is long enough to allow separation of the domains so that two of the polypeptides can assemble into a dimer, making the antibody divalent. These antibody fragments and/or antibody structural variants are obtained using conventional techniques known to those of ordinary skill in the art, and the fragments and structural variants are screened and selected for binding ability to the respective antigen (e.g., PSMA).

Many types of antibodies, or antigen binding portions or derivatives thereof, are useful in the methods and compositions provided herein. The antibodies can be of the various isotypes, including: IgG (e.g., IgG1, IgG2, IgG3, IgG4), IgM, IgA1, IgA2, IgD, or IgE. Preferably, the antibody is an IgG isotype (e.g., IgG1). The antibody molecules can be full-length (e.g., an IgG1 or IgG4 antibody) or can include only an antigen binding portion (e.g., a Fab, F(ab')$_2$, Fv or a single chain Fv fragment). These include monoclonal antibodies, recombinant antibodies, chimeric antibodies, humanized antibodies, deimmunized antibodies, and human antibodies, as well as antigen binding portions of the foregoing. Preferably, the monoclonal antibodies or antigen binding portions or derivatives thereof bind to the extracellular domain of PSMA or portion thereof (e.g., an epitope of PSMA located on the exterior of a cell membrane). Examples of preferred monoclonal antibodies that are capable of binding PSMA include J415, which is produced by the hybridoma cell line having an ATCC Accession Number HB-12101, and J591, which is produced by the hybridoma cell line having an ATCC Accession Number HB-12126.

The antibody or antigen binding portion or derivative thereof can be humanized by methods known in the art. Once the murine antibodies are obtained, the variable regions can be sequenced. The location of the CDRs and framework residues can be determined (see Kabat, E. A., et al. (1991) Sequences of Proteins of Immunological Interest, Fifth Edition, U.S. Department of Health and Human Services, NIH Publication No. 91-3242, and Chothia, C. et al. (1987) J. Mol. Biol. 196:901-917). The light and heavy chain variable regions can, optionally, be ligated to corresponding constant regions.

The antibody or antigen binding portion or derivative thereof may also be modified to delete specific human T cell epitopes (also referred to herein as "deimmunized"). Methods suitable for deimmunizing antibodies are disclosed, for example, in WO 98/52976 and WO 00/34317. Briefly, the heavy and light chain variable regions of the antibody or antigen binding portion or derivative thereof (for example a murine antibody or antigen binding portion or derivative thereof) can be analyzed for peptides that bind to MHC Class II; these peptides represent potential T-cell epitopes (as defined in WO 98/52976 and WO 00/34317). For detection of potential T-cell epitopes, a computer modeling approach can be applied, and in addition a database of human MHC class II binding peptides can be searched for motifs present in the murine $V_H$ and $V_L$ sequences. These motifs bind to any of the 18 major MHC class II DR allotypes, and thus constitute potential T cell epitopes. Any potential T-cell epitopes detected can be eliminated by substituting amino acid residues in the variable regions or by single amino acid substitutions. As far as possible conservative substitutions are made, often but not exclusively, an amino acid common at this position in human germline antibody sequences may be used. Human germline sequences are disclosed in Tomlinson, I. A. et al. (1992) J. Mol. Biol. 227:776-798; Cook, G. P. et al. (1995) Immunol. Today Vol. 16 (5): 237-242; Chothia, D. et al. (1992) J. Mol. Bio. 227:799-817. The V BASE directory provides a comprehensive directory of human immunoglobulin variable region sequences (compiled by Tomlinson, I. A. et al. MRC Centre for Protein Engineering, Cambridge, UK). After the deimmunized $V_H$ and $V_L$ sequences are constructed, the mutagenized variable sequence can, optionally, be fused to a human constant region.

In other embodiments, the antibody or antigen binding portion thereof can have at least one, two, and preferably three CDRs from the light or heavy chain variable region of the J591 antibody produced by the cell line having ATCC Accession Number HB-12126 or the deimmunized J591 (deJ591) antibody produced by the cell line having ATCC Accession Number PTA-3709.

In other embodiments, the antibody or antigen binding portion thereof can have at least one, two and preferably three CDRs from the light or heavy chain variable region of the antibody J415 produced by the cell line having ATCC Accession Number HB-12109 or the deimmunized J415 produced by a cell line having ATCC Accession Number PTA-4174. In still other embodiments, the antibody or antigen binding portion thereof can have at least one, two and preferably three CDRs from the light or heavy chain variable region of the antibody J533 produced by the cell line having ATCC Accession Number HB-12127 or the antibody E99 produced by a cell line having ATCC Accession Number HB-12101.

In some embodiments, the antibody or antigen binding portion or derivative thereof binds all or part of the epitope of an antibody described herein including J591 (produced by the hybridoma HB-12126 deposited at the ATCC), E99 (produced by the hybridoma HB-12101 deposited at the ATCC), J415 (produced by the hybridoma HB-12107 deposited at the ATCC), and J533 (produced by the hybridoma HB-12127 deposited at the ATCC). The antibody or antigen binding portion or derivative thereof can inhibit (e.g., competitively inhibit) the binding of an antibody described herein such as J591, E99, J415, and J533, to human PSMA. In some embodiments, the antibody or antigen binding portion or derivative thereof binds to the epitope recognized by J415. In some embodiments, the antibody or antigen binding portion or derivative thereof binds to the epitope recognized by J591. In some embodiments, the antibody or antigen binding portion or derivative thereof binds to the epitope of E99. In some embodiments, the antibody or antigen binding portion or derivative thereof binds to the epitope recognized by J533.

Whether two antibodies or antigen binding portions or derivatives thereof are capable of specifically binding to the same or overlapping epitopes can be determined using Scatchard analysis and/or competitive binding assays. "Specific binding" of an antibody or antigen binding portion or derivative thereof means that the antibody exhibits sufficient affinity for antigen or a preferred epitope and, preferably, does not exhibit significant cross-reactivity. "Specific binding" includes antibody binding, for example, with an affinity of at least $10^7$, $10^8$, $10^9$, or $10^{10}$ M$^{-1}$. An antibody or antigen binding portion or derivative thereof that does not exhibit significant cross-reactivity is one that will not appreciably bind to an undesirable entity (e.g., an undesirable proteinaceous entity) under conditions suitable to measure antibody specificity. For example, an antibody or antigen binding portion or derivative thereof that specifically binds to PSMA will appreciably bind PSMA but will not significantly react with non-PSMA proteins or peptides. An antibody of antigen binding portion or derivative thereof specific for a preferred epitope will, for example, not significantly cross react with or competitively inhibit the binding to remote epitopes on the same protein or peptide. Antibodies or antigen binding portions or derivatives thereof that recognize the same epitope can be identified in a simple immunoassay showing the ability of one antibody to block the binding of another antibody to a target antigen (e.g., a competitive binding assay). Competitive binding is determined in an assay in which the antibody under test inhibits specific binding of a reference antibody to a common antigen, such as PSMA. Numerous types of competitive binding assays are known, for example: solid phase direct or indirect radioimmunoassay (RIA), solid phase direct or indirect enzyme immunoassay (EIA), sandwich competition assay (see Stahli et al., Methods in Enzymology 9:242 (1983) see also Kim, et al., Infect. Immun. 57:944 (1989)); solid phase direct biotin-avidin EIA (see Kirkland et al., J. Immunol. 137:3614 (1986)); solid phase direct labeled assay, solid phase direct labeled sandwich assay (see Harlow and Lane, Antibodies: A Laboratory Manual, Cold Spring Harbor Press (1988) pp 567-569 and 583); solid phase direct label RIA using 1-125 label (see Morel et al., Mol. Immunol. 25(1):7 (1988)); solid phase direct biotin-avidin EIA (Cheung et al., Virology 176:546 (1990)); direct labeled RIA. (Moldenhauer et al., Scand. J. Immunol. 32:77 (1990); and (Belanger L. et al. Clin. Chim. Acta., 48:15-18 (1973)). Typically, such an assay involves the use of purified antigen bound to a solid surface or cells bearing the antigen, an unlabeled test immunoglobulin and a labeled reference immunoglobulin. Competitive inhibition is measured by determining the amount of label bound to the antigen in the presence of the test antibody relative to the amount of label bound to the antigen in the absence of the test antibody.

EXAMPLES

Example 1

Thirty-two patients were selected for this study. The patients were administered $^{99m}$Tc-MDP, for a standard bone scan, and $^{177}$Lu-J591 on different days. The study was divided into two cohorts. Cohort 1 (n=15) received a $^{177}$Lu-J591 dose of 65 mCi/m$^2$. Cohort 2 (n=17) received a $^{177}$Lu-J591 dose 70 mCi/m$^2$ (e.g., about the maximum tolerated dose). Approximately 3 hours after i.v. administration of $^{99m}$Tc-MDP for a standard bone scan, patients underwent planar radionuclide imaging on a planar gamma camera. Radionuclide bone imaging procedures are well known in nuclear medicine and to those in the art.

Whole body images of were obtained of $^{177}$Lu-J591 and $^{99m}$Tc-MDP for each patient. In addition, patients underwent either a CT scan and/or MR scan to visualize soft tissues not seen on the bone scan. The $^{177}$Lu-J591 images/scans of each patient were blindly scored/graded for targeting of the radiolabel to tumor sites 5-8 days post-treatment. The image grading system measured the intensity of binding or uptake of the targeted $^{177}$Lu-J591 agent. The images were blindly graded as: 0+ for no targeting; 1+ for weak imaging of lesions; 2+ for moderate imaging of lesions; and 3+ for excellent/strong imaging of lesions. PSA levels were also obtained for each patient prior to the administration of $^{177}$Lu-J591 and $^{99m}$Tc-MDP and over the course of the study. After blind scoring, the patients' scores were each compared with the patients' respective PSA response after treatment (e.g., the change in PSA level as a function of time). Disease progression was defined as an increase in PSA of at least 25% PSA from nadir (at least 5 ng/mL) or radiographic progression (1 new bone scan lesion or >20% by RECIST (Response Evaluation Criteria In Solid Tumors) in diameter of a soft tissue lesion or appearance of a new lesion/s.

As shown in FIGS. 1-10, the patients represented a wide spectrum of response to therapy (e.g., antitumor response to $^{177}$Lu-J591) ranging from no response (e.g., continued disease progression) to about a 90% decline in PSA.

Figure 2:
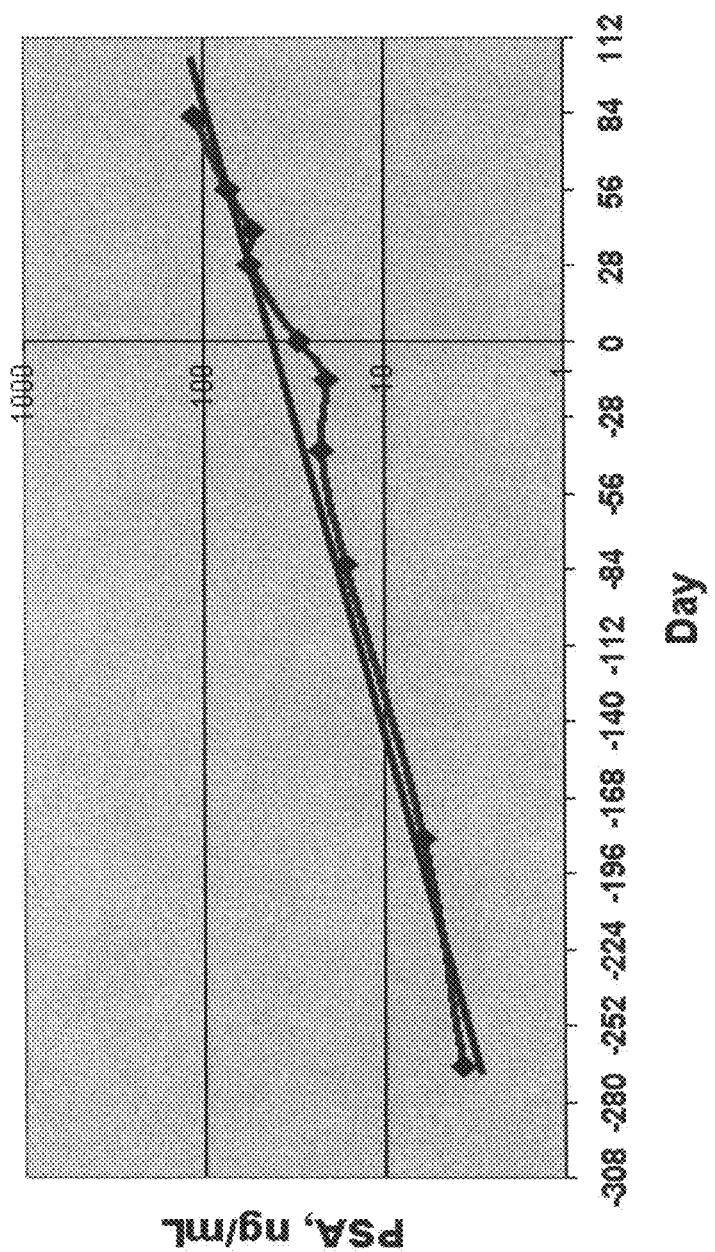
FIG. 2 shows a graph of PSA concentration in blood over time from the patient imaged in FIG. 1. Day 0 represents the treatment date.

FIG. 1 illustrates one patient with a grade 1+ J591 scan (i.e., weak imaging). As shown in the $^{99m}$Tc-MDP bone scan and the $^{177}$Lu-J591 mAb scan, this patient has a large lesion in the right pelvis and several additional lesions on the posterior bone scan (spine, rib, pelvis) that are only weakly imaged in the J591 scan. The treatment (e.g., therapeutic dose of second binding agent) was administered at day 0. The patient's response to the treatment, measured as the change in PSA (ng/mL), is shown in FIG. 2. As shown in FIGS. 1 and 2, the patient did not substantially respond to the treatment (i.e., the trajectory in the PSA was unaffected).

Figure 3:
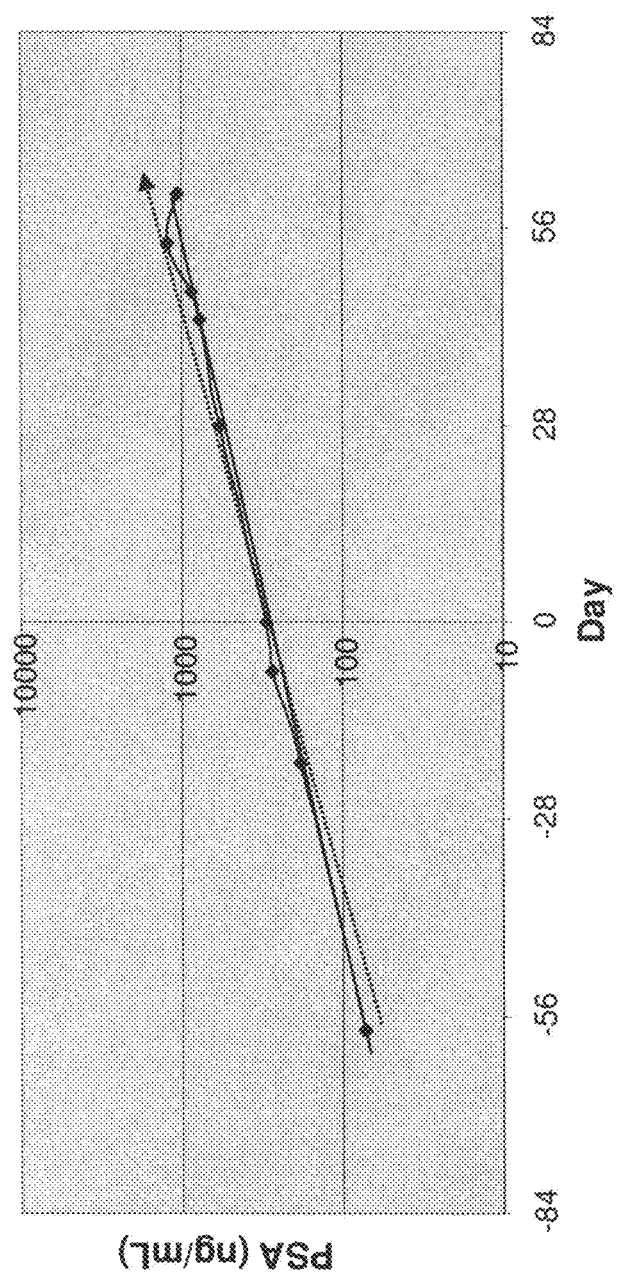
FIG. 3 shows a graph of amount of PSA over time for a patient. Day 0 represents the treatment date.
Figure 4:
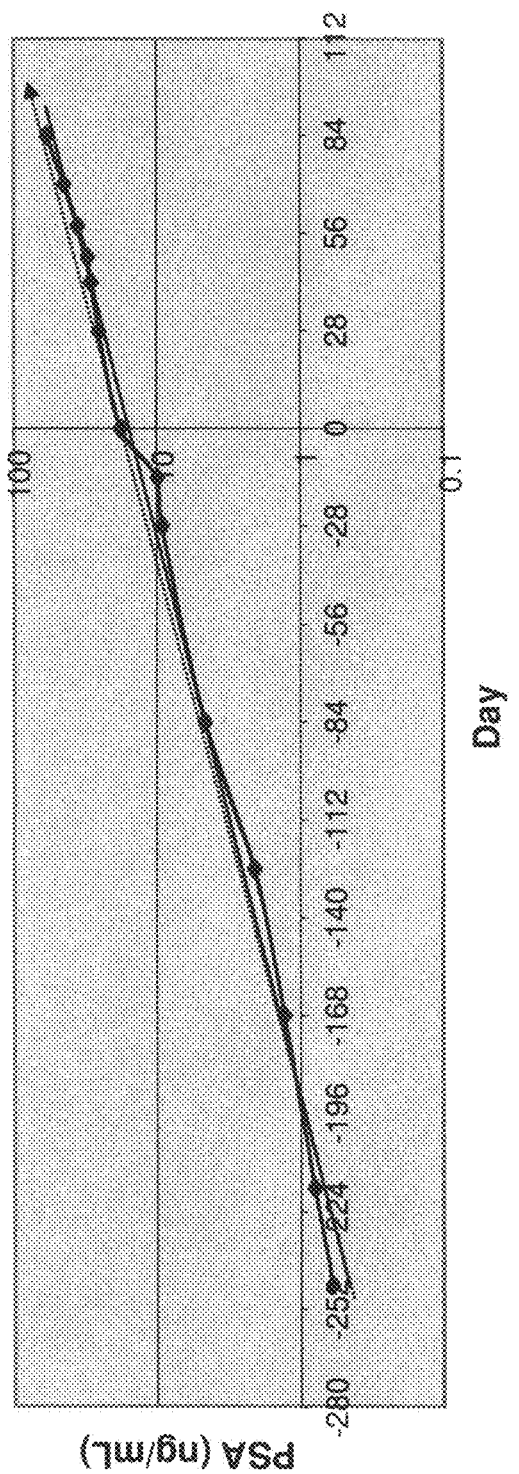
FIG. 4 shows a graph of amount of PSA over time for a patient. Day 0 represents the treatment date.

FIGS. 3 and 4 illustrate the PSA results of two additional patients with grade 1+J591 scans who did not respond to the treatment as measured by change or progression in PSA.

Figure 5:
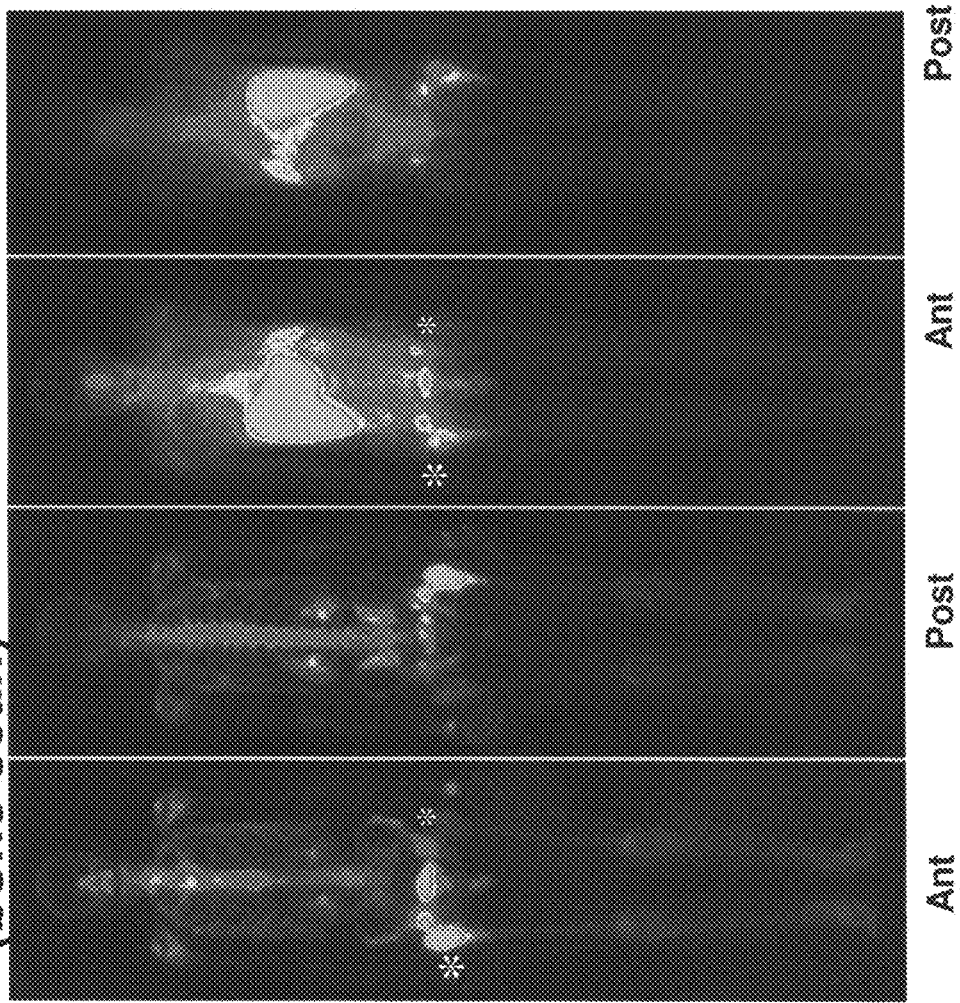
FIG. 5 shows whole body images of scans taken after administration of $^{99m}$Tc-MDP (bone scan) and $^{177}$Lu-J591 mAb (left two and right two images, respectively).

FIG. 5 illustrates a patient with a grade 2+ J591 scan (i.e., moderate imaging). As shown in the $^{99m}$Tc-MDP bone scan and the $^{177}$Lu-J591 mAb scan, this patient has a large lesion in the right hip in the bone scan (denoted by large \*) and a smaller lesion on the left hip (small \*), both of which show moderate imaging intensity. The treatment (e.g., therapeutic dose of second binding agent) was administered at day 0.

Figure 6:
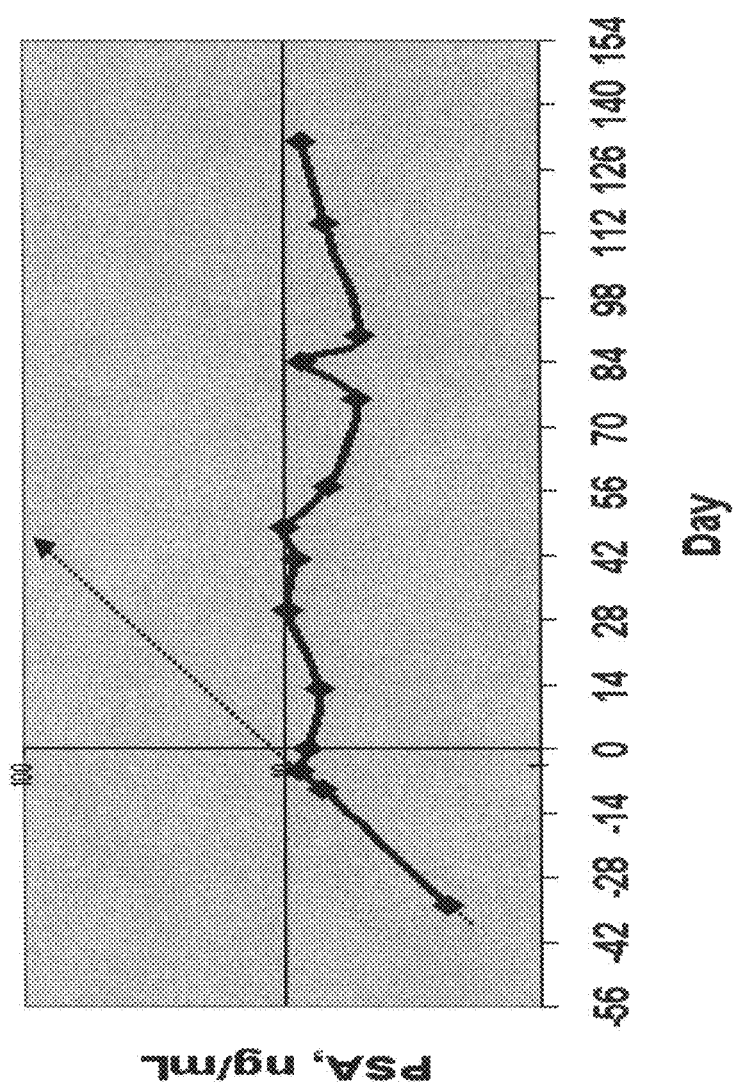
FIG. 6 shows a graph of PSA concentration over time from the patient imaged in FIG. 5. Day 0 represents the treatment date.
Figure 8A:
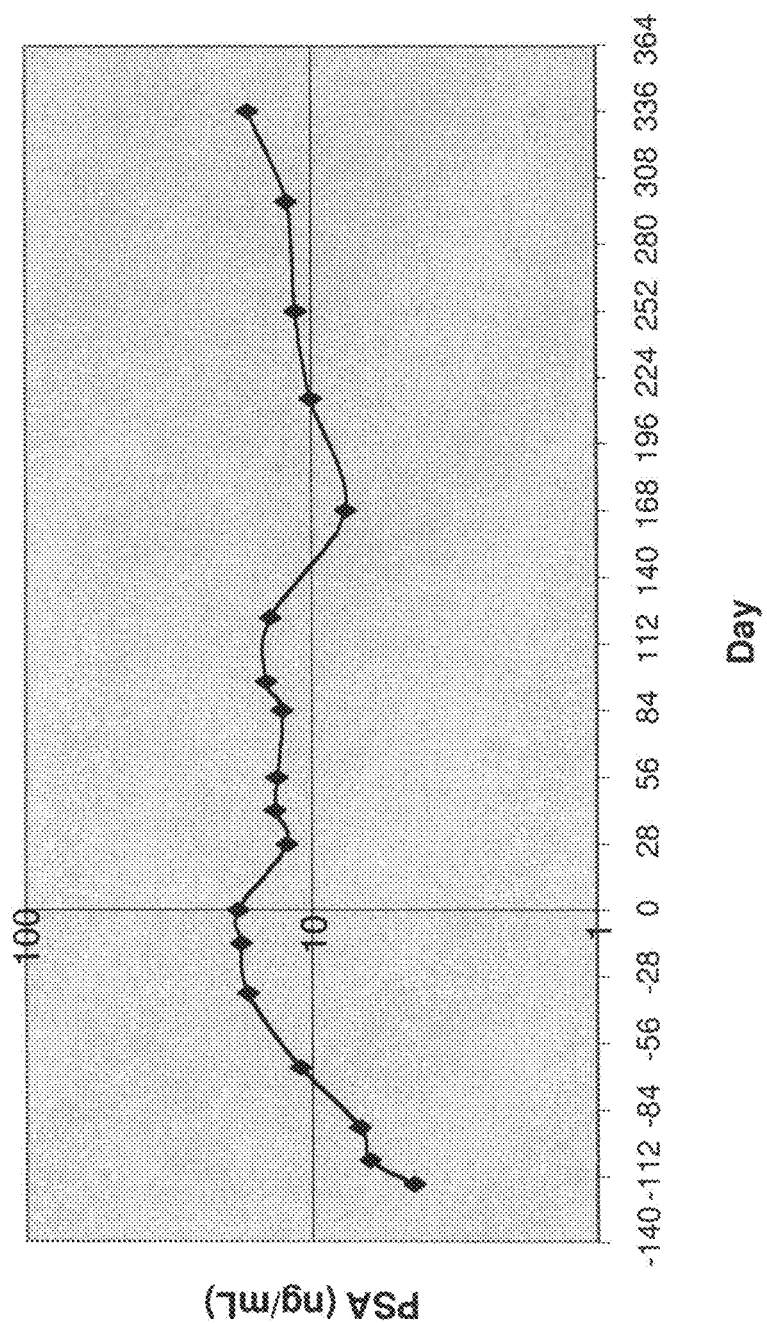
FIGS. 8A and 8B show semi-log and arithmetic graphs of PSA concentration over time from the patient imaged in FIG. 7. Day 0 represents the treatment date.
Figure 8B:
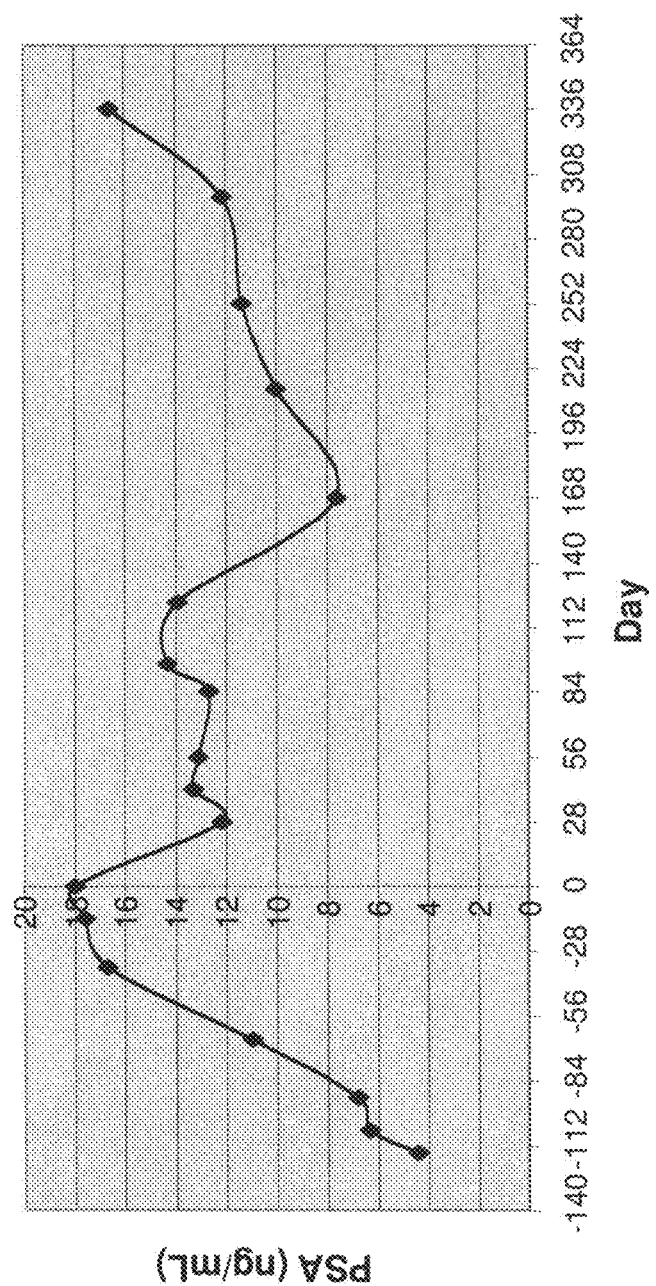

The patient's response to the treatment, measured as the change in PSA is shown in FIG. 6. As shown in FIGS. 5 and 6, the patient exhibited a good response to the treatment (i.e., the PSA concentration stopped increasing at day 0, coincident with administration of the therapeutic dose of second binding agent).

FIG. 7 illustrates another patient with a grade 2+ J591 scan. As shown in the $^{99m}$Tc-MDP bone scan and the $^{177}$Lu-J591 mAb scan, two distinct lesions in the pelvis are well imaged. The treatment (e.g., therapeutic dose of second binding agent) was administered at day 0. The patient's response to the treatment, measured as the change in PSA is also shown in both semi-log (FIG. 8A) and arithmetic (FIG. 8B) plots. The patient exhibited a good response to the treatment (i.e., PSA declined by about 58%).

Figure 9:
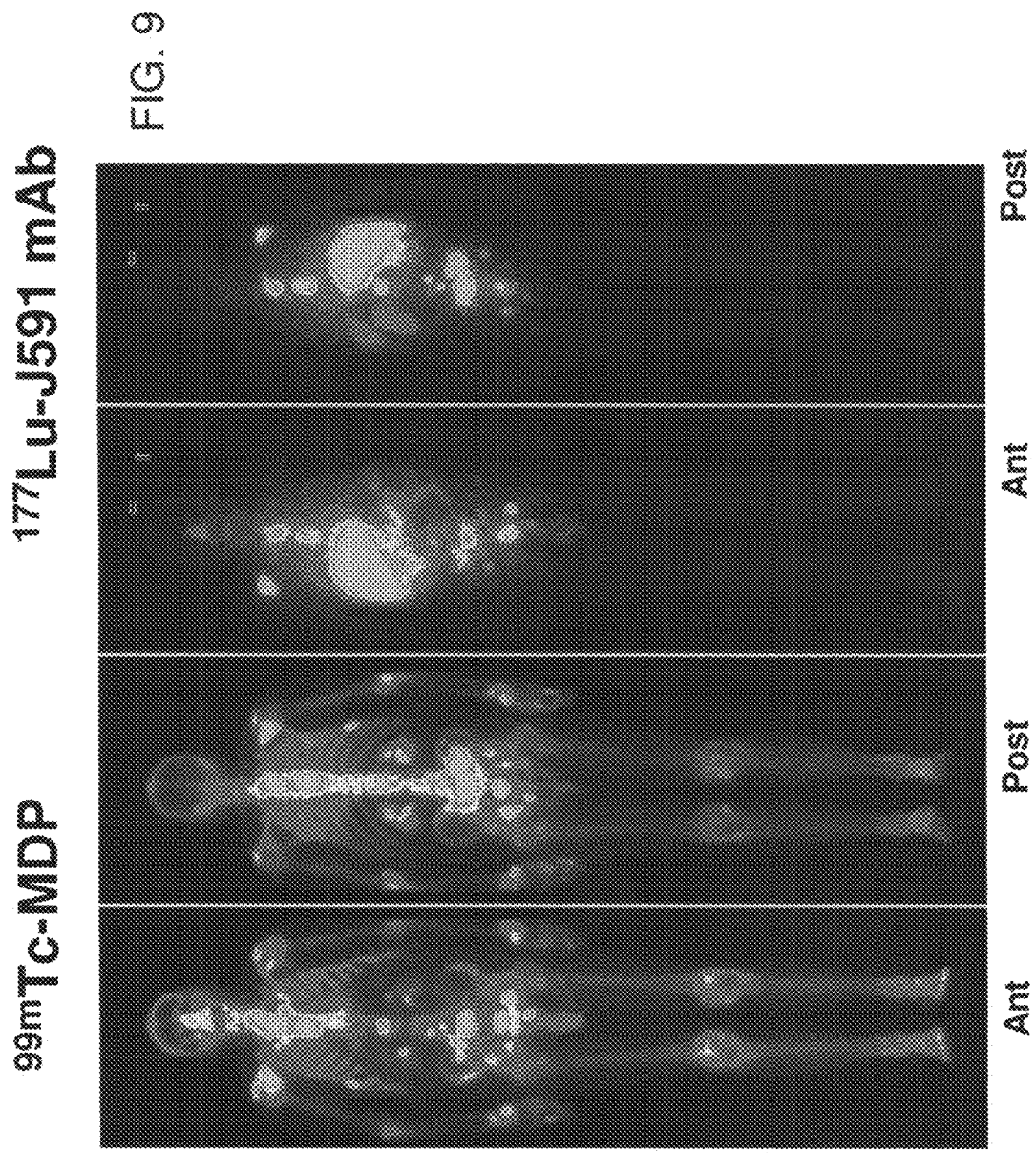
FIG. 9 shows whole body images of scans taken after administration of $^{99m}$Tc-MDP and $^{177}$Lu-J591 mAb (left two and right two images, respectively).
Figure 10A:
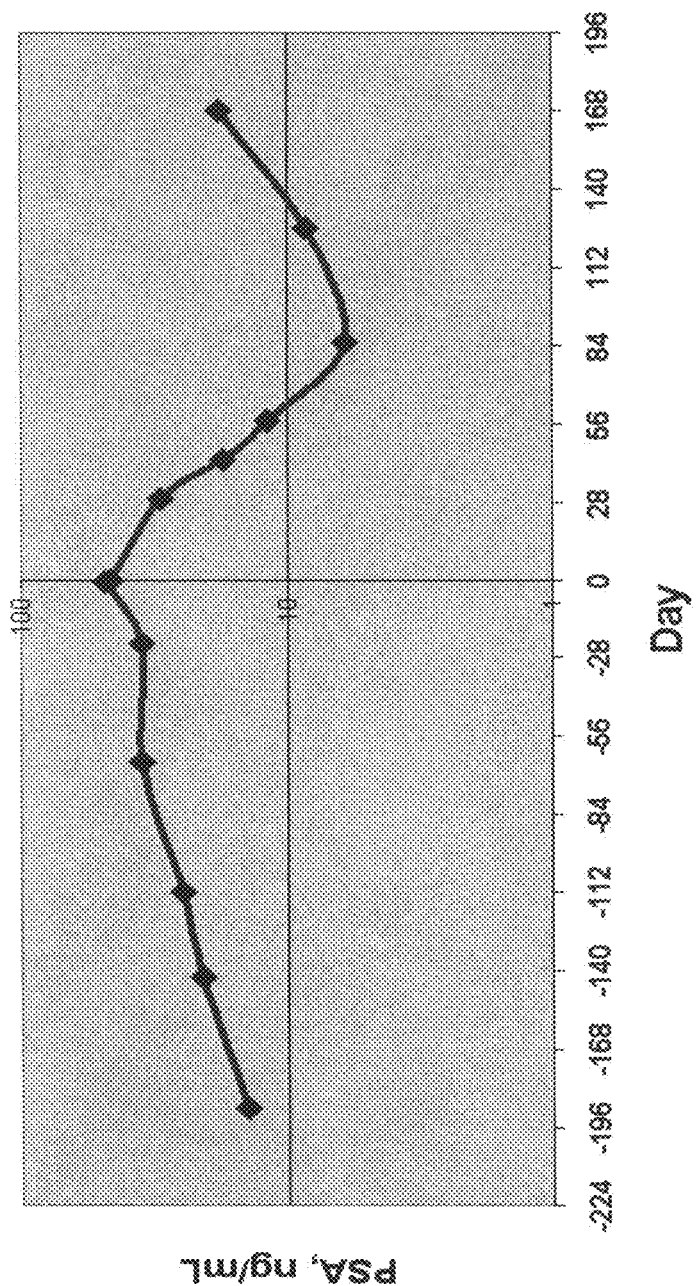
FIGS. 10A and 10B show semi-log and arithmetic graphs of PSA concentration over time from the patient imaged in FIG. 9. Day 0 represents the treatment date.
Figure 10B:
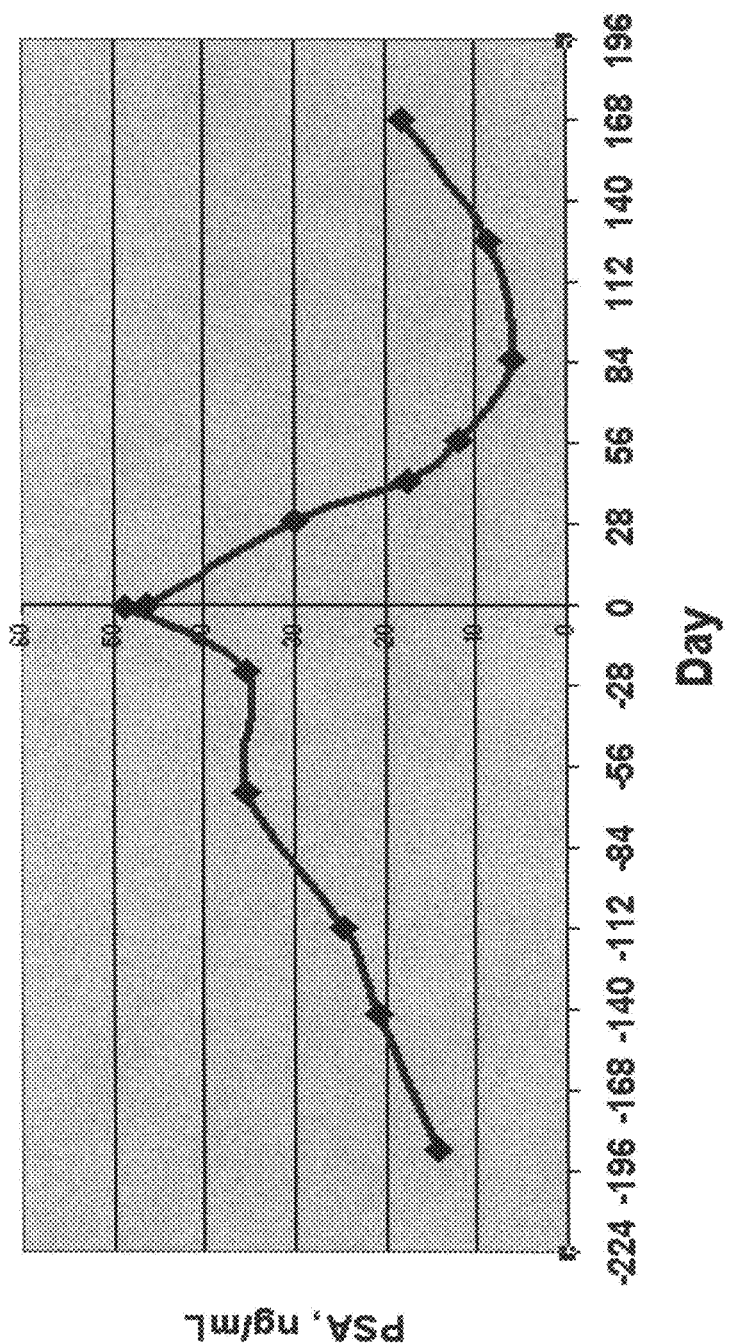

FIG. 9 illustrates a patient with a grade 3+ J591 scan (i.e., excellent/strong imaging). As shown in the $^{99m}$Tc-MDP bone scan and the $^{177}$Lu-J591 mAb scan, multiple distinct, intense lesions are well labeled with J591. The treatment (e.g., therapeutic dose of second binding agent) was administered at day 0. The patient's response to the treatment, measured as the change in PSA is shown in both semi-log (FIG. 10A) and arithmetic (FIG. 10A) plots. The patient exhibited an excellent response to the treatment (i.e., PSA declined by about 90%).

Figure 12:
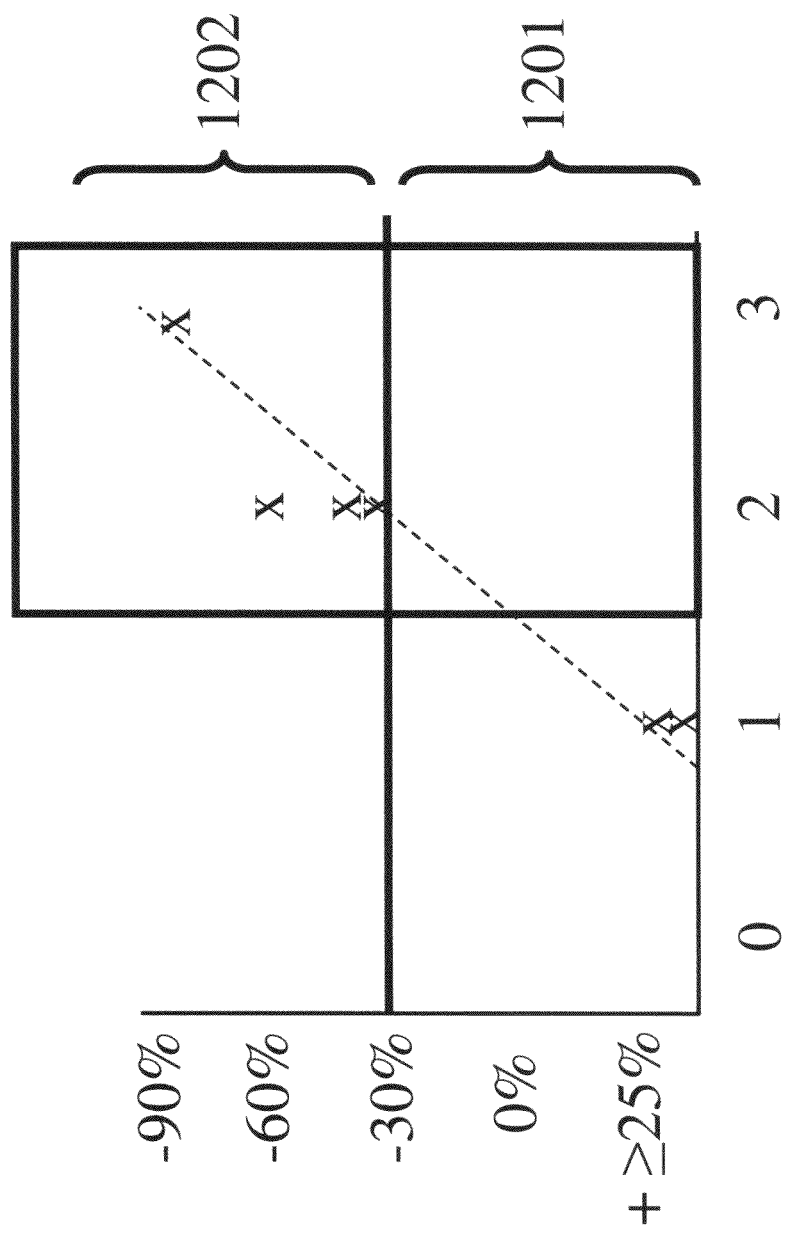
FIG. 12 shows a graph illustrating the relationship between J591 imaging score (0-3+) and PSA response.

FIG. 11 illustrates a relationship between the J591 imaging score and the response after treatment (reflected by PSA change), which allows the prediction of a response to the treatment based upon the score of the J591 scan. FIG. 12 also illustrates a relationship between the J591 imaging score and the PSA response after treatment, which allows the prediction of a response to the treatment based upon the score of the J591 scan (PSA response after treatment shown on the y-axis and score shown on the x axis). In particular, patients with a grade 1+ J591 scan exhibited disease progression (e.g., an increase in PSA, FIG. 12 1201) despite the treatment and patients with a grade 2+ or 3+ scan exhibit significant responses to the treatment (e.g., a decrease in PSA, FIG. 12, 1202).

Example 2

One example of an alternative to the semi-quantitative 0-3+ scoring scale is to calculate a quantitative tumor targeting index (TTI). This can be done on a patient's J591 scan by measuring the count density over the most prominent tumor lesion/s divided by the pixel area of those respective lesions. The lesion count density is then corrected for background count density by doing the same calculation (count density divided by pixel area in the region of interest (ROI) using a lesion-negative area generally in the right anterior thigh). The whole body density is defined as the geometric mean of anterior and posterior imaging counts per pixel. TTI=(lesion ROI count density background count density)/(total body count density). Tumor counts are calculated for a given tumor, over the area of the tumor:

$$T_{cts/area} = \frac{\text{counts\_per\_region}_{tumor}}{\text{region\_area}(px)_{tumor}}$$

Background counts are calculated for a given region, over the area of the region:

$$BG_{cts/area} = \frac{\text{counts\_per\_region}_{background}}{\text{region\_area}(px)_{background}}$$

Body counts are calculated for the anterior and posterior $$Body_{cts/area} = \frac{\sqrt{\text{Counts\_Ant}_{tot\_body} * \text{Counts\_Pos}_{tot\_body}}}{\text{region\_area}(px)_{tot\_body}}$$

$$TTI = (T_{cts/area} - BG_{cts/area}) / Body_{cts/area}$$

Figure 13A:
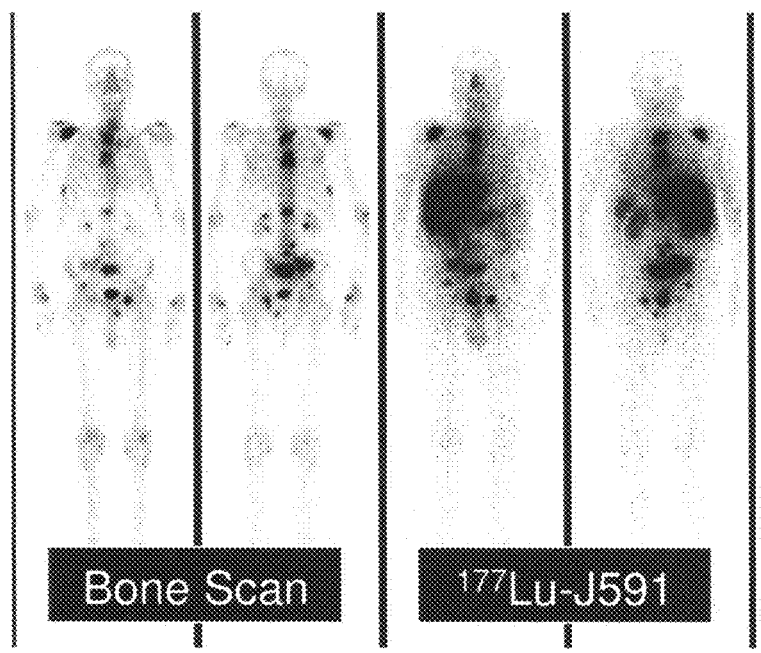
FIGS. 13A and 13B show examples of images quantified using the tumor targeting index (TTI) method.
Figure 13B:
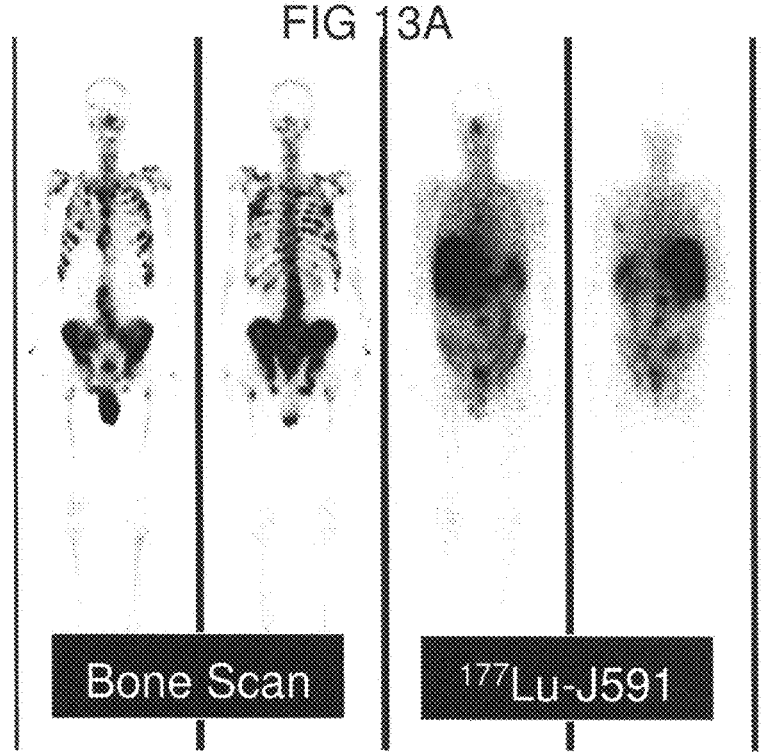

Semi-quantitative tumor-targeting index (TTI) values were measured in a total of 64 lesions and patient response to therapy (PSA reduction or stabilization) was determined. FIG. 13A shows an example of good tumor targeting (the same patient as FIG. 9 and FIG. 10), corresponding to a grade 3 scan (graded as above) and a TTI value of 9.8 (calculated as shown above). FIG. 13B shows an example of poor tumor targeting, corresponding to a grade 1+ scan and a TTI value of 2.4.

PSA reduction or stabilization occurred in 64% of the studied patients. Responders had a mean PSA nadir of 67±24% of baseline. The greatest reduction in PSA was 87%. Of 13 patients with scans graded ≥2, 7 (54%) had PSA reduction, 3 (23%) had stabilization, as shown in Table 1. Of 9 patients with scans graded <2, 2 (22%) had PSA reduction, 2 (22%) had stabilization, as shown in Table 1. The relationship between TTI values of the 64 lesions and treatment response (changes in PSA values) is shown in Table 2.

TABLE 1

$^{177}$Lu-J591 targeting, as measured by graded scans, vs. clinical response.

| Grade | Stabilization | Reduction | Total |
|---|---|---|---|
| ≥2 | 3 (23%) | 7 (54%) | 13 |
| <2 | 2 (22%) | 2 (22%) | 9 |

TABLE 2

$^{177}$Lu-J591 targeting, as measured by TTI, vs. clinical response.

| TTI | Stabilization | Reduction 10-30% | Reduction >30% | Total |
|---|---|---|---|---|
| ≥4 | 5 (25%) | 10 (50%) | 5 (25%) | 20 |
| <3 | 9 (47%) | 9 (47%) | 1 (5%) | 19 |

Example 3: Use of Positron Emission Tomography (PET) for Imaging

Similar to the use of planar imaging as described above, or SPECT (single photon emission computed tomography) imaging, one could also use positron emission tomography (PET) for imaging. PET imaging provides direct, quantitative data reflecting the uptake of the first binding agent. PET imaging can be done with a positron-emitting agent such as $^{124}$Iodine, $^{89}$zirconium, $^{86}$yttrium, or others positron-emitting agent known to those skilled in the art, coupled to the first binding agent. Similar to that described above, the PET-derived quantitative "standard uptake values" (SUVs) allow identification of patients whose lesions demonstrate higher uptake versus those with lower or no uptake. Patients with lesions demonstrating higher SUVs would be predicted to demonstrate higher uptake of the therapeutic second binding agent, in turn, followed by increased likelihood of therapeutic benefit. Use of a directly quantitative imaging modality such as PET obviates the need to visually score the uptake (e.g., 0-3+) or to calculate the TTI as described above. By comparing SUVs of patients who do not respond or benefit from the second therapeutic targeting agent to the SUVs of patients who do respond or benefit to the second therapeutic targeting agent, one of ordinary skill in the art can determine a threshold below which treatment with the second therapeutic agent is of little value as compared to those patients with SUVs above the threshold.

While the invention has been particularly shown and described with reference to specific embodiments, it should be understood by those skilled in the art that various changes in form and detail may be made without departing from the spirit and scope of the invention as defined by the appended claims.

What is claimed is:

1. A method for identifying a patient who is predicted to be responsive to a PSMA-targeted cancer therapy comprising:
   (a) administering a detectably labeled PSMA-binding antibody or antigen-binding fragment thereof that binds to PSMA-expressing cells;
   (b) measuring quantitatively or semi-quantitatively by in vivo imaging the amount of the detectably labeled PSMA-binding antibody or antigen-binding fragment thereof that is bound to PSMA-expressing cells;
   (c) comparing the measured amount of the detectably labeled PSMA-binding antibody or antigen-binding fragment thereof that is bound to PSMA-expressing cells to a predetermined threshold, wherein the predetermined threshold is (1) a visual scoring scale of 2+ or 3+ wherein 2+ is an image or a sample having moderate uptake wherein the detectable tumor uptake is less than that in liver and 3+ is an image or a sample having a strong tumor uptake wherein the detectable tumor uptake is equal to or greater than the amount in liver, or (2) a tumor targeting index (TTI) value of 4 or higher, wherein the TTI index is determined as (lesion region of interest count density−background (lesion negative area) count density)/(total body count density);
   (d) selecting the patient for a PSMA-targeted cancer therapy if the measured amount meets or exceeds the predetermined threshold;
   wherein the patient has not previously been administered a PSMA-targeted cancer therapy; and
   wherein the detectably labeled PSMA-binding antibody or antigen-binding fragment thereof that binds to PSMA expressing cells is selected from the group consisting of J415, J591, E99, and J533, and
   (e) administering a PSMA-targeted cancer therapy to the selected patients, wherein the selected patients show a decrease in PSA level within 28 days post the administration of PSMA-targeted cancer therapy.

2. The method of claim 1, wherein the PSMA-binding antibody or antigen-binding fragment thereof has an affinity of at least about $10^{-9}$ M for the PSMA target.

3. The method of claim 1, wherein the detectably labeled PSMA-binding antibody or antigen-binding fragment thereof that binds to PSMA-expressing cells is detected by radioscintigraphy, magnetic resonance imaging (MRI), computed tomography (CT) scan, or positron emission tomography (PET).

4. The method of claim 1, wherein the patient has prostate cancer.

5. The method of claim 1, wherein the patient has a non-prostate cancer which contains PSMA-expressing neovasculature.

6. The method of claim 1, wherein the detectably labeled PSMA-binding antibody or antigen-binding fragment thereof that binds to PSMA-expressing cells incorporates a radiolabel.

7. The method of claim 6, wherein the radiolabel is selected from the group consisting of $^{177}$Lu, $^{111}$In, $^{67}$Cu, $^{64}$Cu, $^{18}$F, $^{99m}$Tc, $^{124}$I, $^{125}$I, $^{68}$Ga, and $^{89}$Zr.

8. The method of claim 1, wherein the PSMA-binding antibody or antigen-binding fragment thereof that binds to PSMA-expressing cells comprises a positron emission tomography (PET) detection agent.

9. The method of claim 1, wherein the PSMA-targeted cancer therapy comprises a PSMA-binding antibody or antigen-binding fragment thereof that is conjugated to a cytotoxic agent or radioisotope.

* * * * *